United States Patent
Arnold et al.

(10) Patent No.: US 6,177,263 B1
(45) Date of Patent: *Jan. 23, 2001

(54) RECOMBINATION OF POLYNUCLEOTIDE SEQUENCES USING RANDOM OR DEFINED PRIMERS

(75) Inventors: Frances H. Arnold; Zhixin Shao, both of Pasadena, CA (US); Joseph A. Affholter, Midland, MI (US); Huimin Zhao; Lorraine J. Giver, both of Pasadena, CA (US)

(73) Assignee: California Institute of Technology, Pasadena, CA (US)

(*) Notice: Under 35 U.S.C. 154(b), the term of this patent shall be extended for 0 days.

This patent is subject to a terminal disclaimer.

(21) Appl. No.: 09/353,556

(22) Filed: Jul. 14, 1999

Related U.S. Application Data

(60) Division of application No. 08/905,359, filed on Aug. 4, 1997, and a continuation-in-part of application No. 08/905,058, filed on Aug. 1, 1997, now abandoned

(60) Provisional application No. 60/041,666, filed on Mar. 25, 1997, provisional application No. 60/045,211, filed on Apr. 30, 1997, and provisional application No. 60/046,256, filed on May 12, 1997.

(51) Int. Cl.[7] .................... C12P 19/34; C12N 15/09; C12Q 1/68
(52) U.S. Cl. .................... 435/91.1; 435/6; 435/69.1; 435/91.2
(58) Field of Search .................... 435/6, 91.1, 91.2, 435/69.1, 440, 455, 471, 489

(56) References Cited

U.S. PATENT DOCUMENTS

| | | | |
|---|---|---|---|
| 4,683,202 | * | 7/1987 | Mullis . |
| 4,800,159 | * | 1/1989 | Mullis et al. . |
| 4,965,188 | * | 10/1990 | Mullis et al. . |
| 4,994,368 | * | 2/1991 | Goodman et al. . |
| 4,994,379 | * | 2/1991 | Chang . |
| 5,023,171 | * | 6/1991 | Ho et al. . |
| 5,043,272 | * | 8/1991 | Hartley . |
| 5,093,257 | * | 3/1992 | Gray . |
| 5,176,995 | * | 1/1993 | Sninsky et al. . |
| 5,187,083 | * | 2/1993 | Mullis . |
| 5,223,408 | * | 6/1993 | Goeddel et al. . |
| 5,234,824 | * | 8/1993 | Mullis . |
| 5,264,563 | * | 11/1993 | Huse . |
| 5,279,952 | * | 1/1994 | Wu . |
| 5,316,935 | * | 5/1994 | Arnold et al. . |
| 5,356,801 | * | 10/1994 | Rambosek et al. . |
| 5,360,728 | * | 11/1994 | Prasher . |
| 5,418,149 | * | 5/1995 | Gelfand et al. . |
| 5,422,266 | * | 6/1995 | Cormier et al. . |
| 5,489,523 | * | 2/1996 | Mathur . |
| 5,502,167 | * | 3/1996 | Waldmann et al. . |
| 5,512,463 | * | 4/1996 | Stemmer . |
| 5,514,568 | * | 5/1996 | Stemmer . |
| 5,521,077 | * | 5/1996 | Khosla et al. . |
| 5,523,388 | * | 6/1996 | Huse . |
| 5,541,309 | * | 7/1996 | Prasher . |
| 5,556,750 | * | 9/1996 | Modrich et al. . |
| 5,556,772 | * | 9/1996 | Sorge et al. . |
| 5,605,793 | * | 2/1997 | Stemmer . |
| 5,629,179 | * | 5/1997 | Mierendorf et al. . |
| 5,652,116 | * | 7/1997 | Grandi et al. . |
| 5,679,522 | * | 10/1997 | Modrich et al. . |
| 5,698,426 | * | 12/1997 | Huse . |
| 5,714,316 | * | 2/1998 | Weiner et al. . |
| 5,723,323 | * | 3/1998 | Kauffman et al. . |
| 5,756,316 | * | 5/1998 | Schellenberger . |
| 5,763,192 | * | 6/1998 | Kauffman et al. . |
| 5,770,434 | * | 6/1998 | Huse . |
| 5,773,267 | * | 6/1998 | Jacobs et al. . |
| 5,783,431 | * | 7/1998 | Peterson et al. . |
| 5,795,747 | * | 8/1998 | Henco et al. . |
| 5,808,022 | * | 9/1998 | Huse . |
| 5,811,238 | * | 9/1998 | Stemmer et al. . |
| 5,814,476 | * | 9/1998 | Kauffman et al. . |
| 5,817,483 | * | 10/1998 | Kauffman et al. . |
| 5,824,469 | * | 10/1998 | Horwitz et al. . |
| 5,824,485 | * | 10/1998 | Thompson et al. . |
| 5,824,514 | * | 10/1998 | Kauffman et al. . |
| 5,830,696 | * | 11/1998 | Short . |
| 5,830,721 | * | 11/1998 | Stemmer et al. . |
| 5,834,252 | * | 11/1998 | Stemmer et al. . |

(List continued on next page.)

FOREIGN PATENT DOCUMENTS

| | | | |
|---|---|---|---|
| 0 252 666 | * | 1/1988 | (EP) . |
| 552 266 | * | 7/1993 | (EP) . |
| 544 809 B1 | * | 12/1998 | (EP) . |
| 563 296 B1 | * | 3/1999 | (EP) . |

(List continued on next page.)

OTHER PUBLICATIONS

Andersson et al., "Muller's ratchet decreases fitness of a DNA–based microbe", *PNAS*, 93: 906–907 (Jan. 1996).*

(List continued on next page.)

* cited by examiner

*Primary Examiner*—Robert A. Schwartzman
*Assistant Examiner*—Thomas G. Larson
(74) *Attorney, Agent, or Firm*—Townsend and Townsend and Crew LLP

(57) ABSTRACT

A method for in vitro mutagenesis and recombination of polynucleotide sequences based on polymerase-catalyzed extension of primer oligonucleotides is disclosed. The method involves priming template polynucleotide(s) with random-sequences or defined-sequence primers to generate a pool of short DNA fragments with a low level of point mutations. The DNA fragments are subjected to denaturization followed by annealing and further enzyme-catalyzed DNA polymerization. This procedure is repeated a sufficient number of times to produce full-length genes which comprise mutants of the original template polynucleotides. These genes can be further amplified by the polymerase chain reaction and cloned into a vector for expression of the encoded proteins.

41 Claims, 14 Drawing Sheets

U.S. PATENT DOCUMENTS

| | | | |
|---|---|---|---|
| 5,837,458 | * | 11/1998 | Minshull et al. . |
| 5,851,813 | * | 12/1998 | Desrosiers . |
| 5,858,725 | * | 1/1999 | Crowe et al. . |
| 5,871,974 | * | 2/1999 | Huse . |
| 5,928,905 | * | 7/1999 | Stemmer et al. . |
| 5,939,250 | * | 8/1999 | Short . |
| 5,955,358 | * | 9/1999 | Huse . |
| 5,958,672 | * | 9/1999 | Short . |
| 5,965,408 | * | 10/1999 | Short . |
| 5,965,415 | * | 10/1999 | Radman et al. . |
| 5,976,862 | * | 11/1999 | Kauffman et al. . |

FOREIGN PATENT DOCUMENTS

| | | | |
|---|---|---|---|
| WO 90/07576 | * | 7/1990 | (WO) . |
| WO 90/14424 | * | 11/1990 | (WO) . |
| WO 90/14430 | * | 11/1990 | (WO) . |
| WO 91/01087 | * | 2/1991 | (WO) . |
| WO 91/06570 | * | 5/1991 | (WO) . |
| WO 91/07506 | * | 5/1991 | (WO) . |
| WO 91/15581 | * | 10/1991 | (WO) . |
| WO 91/16427 | * | 10/1991 | (WO) . |
| WO 92/06176 | * | 4/1992 | (WO) . |
| WO 92/07075 | * | 4/1992 | (WO) . |
| WO 92/18645 | * | 10/1992 | (WO) . |
| WO 93/02191 | * | 2/1993 | (WO) . |
| WO 93/06213 | * | 4/1993 | (WO) . |
| WO 93/11237 | * | 6/1993 | (WO) . |
| WO 93/15208 | * | 8/1993 | (WO) . |
| WO 93/16192 | * | 8/1993 | (WO) . |
| WO 93/18141 | * | 9/1993 | (WO) . |
| WO 93/25237 | * | 12/1993 | (WO) . |
| WO 94/03596 | * | 2/1994 | (WO) . |
| WO 94/09817 | * | 5/1994 | (WO) . |
| WO 94/11496 | * | 5/1994 | (WO) . |
| WO 94/13804 | * | 6/1994 | (WO) . |
| WO 95/17413 | * | 6/1995 | (WO) . |
| WO 95/22625 | * | 8/1995 | (WO) . |
| WO 96/33207 | * | 10/1996 | (WO) . |
| WO 97/07205 | * | 2/1997 | (WO) . |
| WO 97/20078 | * | 6/1997 | (WO) . |
| WO 97/25410 | * | 7/1997 | (WO) . |
| WO 97/35966 | * | 10/1997 | (WO) . |
| WO 98/01581 | * | 1/1998 | (WO) . |
| WO 98/27230 | * | 6/1998 | (WO) . |
| WO 98/28416 | * | 7/1998 | (WO) . |
| WO 98/41622 | * | 9/1998 | (WO) . |
| WO 98/41623 | * | 9/1998 | (WO) . |
| WO 98/41653 | * | 9/1998 | (WO) . |
| WO 98/42832 | * | 10/1998 | (WO) . |

OTHER PUBLICATIONS

Arkin et al., "An Algorithm for Protein Engineering: Simulations of Recursive Ensemble Mutagenesis" Proc. Natl. Acad. Sci. USA, 89(16):7811–7815 (1992).*

Atreya et al., "Construction of in–frame chimeric plant genes by simplified PCR strategies," Plant Mol. Biol., 19:517–522 (1992).*

Balint et al., "Antibody Engineering By Parsimonious Mutagenesis", Gene, 137(1):109–118 (1993).*

Bailey, "Toward a Science of Metabolic Engineering", Science, 252: 1668–1680 (1991).*

Barrett et al., "Genotypic analysis of multiple loci in somatic cells by whole genome amplification", Nuc. Acids Res., 23(17): 3488–3492 (1995).*

Bartel et al., "Isolation of New Ribozymes From a Large Pool of Random Sequences", Science, 261:1411–1418 (1993).*

Beaudry et al., "Directed Evolution of an RNA Enzyme," Science, 257:635–641 (1992).*

Berger et al., "Phoenix Mutagenesis: One–Step Reassembly of Multiply Cleaved Plasmids With Mixtures of Mutant and Wild–Type Fragments," Anal. Biochem., 214:571–579 (1993).*

Berkhout et al., "In Vivo Selection of Randomly Mutated Retroviral Genomes," Nucleic Acids Research, 21(22):5020–5024 (1993).*

Bock et al., "Selection of single–stranded DNA molecules that bind and inhibit human thrombin," Nature, 355:564–566 (Feb. 2, 1992).*

Cadwell et al., "Randomization of Genes by PCR Mutagenesis," PCR Methods and Applications, 2:28–33 (1992).*

Calogero et al., "In Vivo Recombination and the Production of Hybrid Genes," Microbiology Letters, 76:41–44 (1992).*

Cameron et al., "Cellular and Metabolic Engineering An Overview", Applied Biochem. Biotech., 38: 105–140 (1993).*

Caren et al., "Efficient Sampling of Protein Sequence Space for Multiple Mutants," Biotechnology, 12(5):517–520 (1994).*

Chakrabarty, "Microbial Degradation of Toxic Chemicals: Evolutionary Insights and Practical Considerations", ASM News, 62(3): 130–137 (1996).*

Chater, "The Improving Prospects for Yield Increase by Genetic Engineering in Antibiotic–Producing Streptomycetes", Biotechnology, 8: 115–121 (Feb. 1990).*

Chen et al., "Tuning the activity of an enzyme for unusual environments: Sequential random mutagenesis of subtilisin E for catalysis in dimethylformamide", PNAS, 90: 5618–5622 (Jun. 1993).*

Clackson et al., "Making antibody fragments using phage display libraries," Nature, 352:624–628 (Aug. 15, 1991).*

Crameri et al., "Combinatorial Multiple Cassette Mutagenesis Creates All The Permutations Of Mutant And Wild–Type Sequences", Biotechniques, 18(2):194–196 (1995).*

Crameri et al., "Improved Green Fluorescent Protein By Molecular Evolution Using DNA Shuffling", Nat. Biotechnol., 14(3):315–319 (1996).*

Crameri et al., "Construction And Evolution Of Antibody–Phage Libraries By DNA Shuffling", Nat. Med., 2(1):100–102 (1996).*

Crameri et al., "Molecular Evolution Of An Arsenate Detoxification Pathway By DNA Shuffling", Nat. Biotechnol., 15(5):436–438 (1997).*

Crameri et al., "DNA Shuffling Of A Family Of Genes From Diverse Species Accelerates Directed Evolution", Nature, 391(3664):288–291 (1998).*

Crameri et al., "10(20)–Fold aptamer library amplification without gel purification," Nuc. Acids Res., 21(18):4410 (1993).*

Cull et al., "Screening for receptor ligands using large libraries of peptides linked to the C terminus of the lac repressor," PNAS, 89:1865–1869 (Mar. 1992).*

Cwirla et al., "Peptides on phage: A vast library of peptides for identifying ligands," PNAS, 87:6378–6382 (Aug. 1990).*

Daugherty et al., "Polymerase chain reaction facilitates the cloning, CDR–grafting, and rapid expression of a murine monoclonal antibody directed against the CD18 component of leukocyte integrins," Nuc. Acids Res., 19(9):2471–2476 (1991).*

Delagrave et al., "Recursive Ensemble Mutagenesis," *Protein Engineering*, 6(3):327–331 (1993).*

Delagrave et al., "Searching Sequence Space to Engineer Proteins: Exponential Ensemble Mutagenesis," *Biotechnology*, 11:1548–1552 (Dec. 1993).*

Dieffenbach et al., *PCR Primer, A Laboratory Manual*, Cold Spring Harbor Laboratory Press, pp. 583–589, 591–601, 603–612, and 613–621 (1995).*

Dube et al., "Artificial mutants Generated by the Insertion of Random Oligonucleotides into the Putative Nucleoside Binding Site of the HSV-1 Thymidine Kinase Gene," *Biochemistry*, 30(51):11760–11767 (1991).*

Evnin et al., "Substrate specificity of trypsin investigated by using a genetic selection", *PNAS*, 87: 6659–6663 (Sep. 1990).*

Fang et al., "Human Strand–specific Mismatch Repair Occurs by a Bidirectional Mechanism Similar to That of the Bacterial Reaction", *J. Biol. Chem.*, 268(16): 11838–11844 (Jun. 5, 1993).*

Feinberg et al., "A Technique for Radiolabeling DNA Restriction Endonuclease Fragments to High Specific Activity," *Anal. Biochem.*, 132:6–13 (1983).*

Fisch et al., "A Strategy Of Exon Shuffling For Making Large Peptide Repertoires Displayed On Filamentous Bacteriophage", *Proc Natl Acad Sci USA*, 93(15):7761–7766 (1996).*

Fullen et al., "Genetic Algorithms and Recursive Ensemble Mutagenesis in Protein Engineering," *Complexity Int.'l 1994 I*, printed from website http://www.csu.edu.au/ci/vol1/fuellen/REM.html on Dec. 7, 1999.*

Gates et al., "Affinity Selective Isolation Of Ligands From Peptide Libraries Through Display On A Lac Repressor 'Headpiece Dimer'",*J. Mol. Biol.*, 255(3):373–386 (1996).*

Ghosh et al., "Arginine–395 Is Required for Efficient in Vivo and in Vitro Aminoacylation of tRNAs by *Escherichia coli* Methionyl–tRNA Stnthetase," *Biochemistry*, 30:11767–11774 (1991).*

Goldman et al., "An Algorithmically Optimized Combinatorial Library Screened by digital Imaging Spectroscopy," *Biotechnology*, 10:1557–1561 (Dec. 1992).*

Gram et al., "In Vitro Selection and Affinity Maturation of Antibodies From a Naïve Combinatorial Immunoglobulin Library", *Proc. Natl. Acad. Sci. USA*, 89:3576–3580 (1992).*

Greener et al., "An Efficient Random Mutagenesis Technique Using An *E. coli* Mutator Strain", *Methods in Molecular Biology*, 57:375–385 (1995).*

Harlow et al., "Construction of Linker–Scanning Mutations using the Polymerase Chain Reaction," *Methods in Mol. Biol.*, 31:87–96 (1994).*

Heda et al., "A simple in vitro site directed mutagenesis of concatamerized cDNA by inverse polymerase chain reaction," *Nuc. Acids Res.*, 20(19):5241–5242 (1992).*

Heim et al., "Wavelength Mutations And Posttranslational Autoxidation Of Green Fluorescent Protein", *Proc. Natl. Acad. Sci. USA*, 91(26):12501–12504 (1994).*

Hermes et al., "Searching Sequence Space by Definably Random Mutagenesis: Improving the Catalytic Potency of an Enzyme," *Proc. Natl. Acad. Sci. USA*, 87(2):696–700 (1990).*

Ho et al., "DNA and Protein Engineering Using the Polymerase Chain Reaction: Splicing by Overlap Extension," *DNA and Protein Eng. Techniques*, 2(2):50–55 (1990).*

Ho et al., "Site–Directed Mutagenesis by Overlap Extension Using the Polymerase Chain Reaction," *Gene*, 77:51–59 (1989).*

Hodgson, "The Whys and Wherefores of DNA Amplification," *Biotechnology*, 11:940–942 (Aug. 1993).*

Horton et al., "Engineering Hybrid Genes Without the Use of Restriction Enzymes: Gene Splicing by Overlap Extension," *Gene*, 77:61–68 (1989).*

Horton et al., "Gene Splicing by Overlap Extension: Tailor–Made Genes Using the Polymerase chain Reaction," *BioTechniques*, 8(5):528–535 (May 1990).*

Horton et al., "Gene Splicing by Overlap Extension," *Mehtods in Enzymology*, 217:270–279 (1993).*

Ippolito et al., "Structure assisted redesign of a protein–zinc–binding site with femtomolar affinity", *PNAS*, 92: 5017–5021 (May 1995).*

Jayaraman et al., "Polymerase chain reaction–mediated gene synthesis: Synthesis of a gene coding for isozyme c of horseradish peroxidase," *PNAS*, 88:4084–4088 (May 1991).*

Jones et al., "A Rapid Method for Recombination and Site–Specific Mutagenesis by Placing Homologous ends on DNA Using Polymerase Chain Reaction," *BioTechniques*, 10(1): 62–66, (1991).*

Jones et al., "Recombinant Circle PCR and Recombination PCR for Site–Specific Mutagenesis Without PCR Product Purification," *Biotechniques* 12(4):528–534 (1992).*

Joyce, G. F., "Directed Molecular Evolution," *Scientific American*, (Dec. 1992).*

Kellogg et al., "Plasmid–Assisted Molecular Breeding: New Technique for Enhanced Biodegradation of Persistent Toxic Chemicals", *Science*, 214: 1133–1135 (Dec. 4, 1981).*

Kim et al., "Human Immunodeficiency Virus Reverse Transcriptase," *The Journal of Biological Chemistry*, 271(9):4872–4878 (1996).*

Klug et al., "Creating chimeric molecules by PCR directed homologous DNA recombination," *Nuc. Acids Res.*, 19(10):2793 (1991).*

Krishnan et al., "Direct and crossover PCR amplification to facilitate Tn5supF–based sequencing of λ phage clones," *Nuc. Acids Res.*, 19(22):6177–6182 (1991).*

Kunkel, "Rapid and efficient site–specific mutagenesis without phenotypic selection", *PNAS*, 82: 488–493 (Jan. 1985).*

Leung et al., "A Method For Random Mutagenesis of a Defined DNA Segment Using a Modified Polymerase Chain Reaction," *Techniques*, 1:11–15 (1989).*

Levichkin et al., "A New Approach to Construction of Hybrid Genes: Homolog Recombination Method", *Mol. Biology*, 29(5) part 1: 572–577 (1995).*

Lewis et al., "Efficient site directed in vitro mutagenesis using ampicillin selection", *Nuc. Acids Res.*, 18(21): 3439–3443 (1990).*

Lowman, H.B. et al, "Affinity Maturation of Human Growth Hormone by Monovalent Phage Display," *J. Mol. Biol.*, 234:564–578 (1993).*

Majumder, K., "Ligation–free gene synthesis by PCR: synthesis and mutagenesis at multiple loci of a chimeric gene encoding OmpA signal peptide and hirudin," *Gene*, 110:89–94 (1992).*

Marks et al., "By–passing Immunization, Human Antibodies from V–gene Libraries Displayed on Phage," *J. Mol. Biol.*, 222:581–597 (1991).*

Marks et al., "By–Passing Immunization: Building High Affinity Human Antibodies by Chain Shuffling," *Bio/Technology*, 10:779–783 (1992).*

Marton et al., "DNA Nicking Favors PCR Recombination", *Nucleic Acids Res.*, 19(9):2423–2426 (1991).*

McCafferty et al., "Phage antibodies: filamentous phage displaying antibody variable domains," *Nature*, 348:552–554 (Dec. 6, 1990).*

Meyerhans et al., "DNA Recombination During PCR," *Nucleic Acids Research*, 18(7):1687–1691 (1990).*

Moore et al., "Directed evolution of a para–nitrobenzyl esterase for aqueous–organic solvents", *Nature Biotech.*, 14: 458–467 (Apr. 1996).*

Morl et al., "Group II intron RNA–catalyzed recombination of RNA in vitro," *Nuc. Acids Res.*, 18(22):6545–6551 (1990).*

Mullis et al., "Specific Synthesis of DNA in Vitro via a Polymerase–Catalyzed Chain Reaction," *Methods in Enzymology*, 155:335–351 (1987).*

Mullis et al., "Specific Enzymatic Amplification of DNA In Vitro: The Polymerase Chain Reaction," Cold Spring Harbor Symposia on Quantitative Biology, 51:263–273 (1986).*

Near, "Gene Conversion Of Immunoglobulin Variable Regions In Mutagenesis Cassettes By Replacement PCR Mutagenesis", *Biotechniques*, 12(1):88–97 (1992).*

Nissim et al., "Antibody fragments from a 'single pot' display library as immunochemical reagents," *EMBO Journal*, 13(3):692–698 (1994).*

Oliphant et al., "Cloning of Random–Sequence Oligodeoxynucleotides," *Gene*, 44(2–3):177–183 (1986).*

Omura, "Philosophy of New Drug Discovery", *Microbiol. Rev.*, 50(3): 259–279 (Sep. 1986).*

Osuna et al., "Combinatorial mutagenesis of three major groove–contacting residues of Eco RI: single and double amino acid replacements retaining methyltransferase–sensitive activities," *Gene*, 106:7–12 (1991).*

Paabo et al., "DNA Damage Promotes Jumping between Templates during Enzymatic Amplification," *J. Biol. Chem.*, 265(8):4718–4721 (Mar. 15, 1990).*

Perlak, "Single Step Large Scale Site–Directed In Vitro Mutagenesis Using Multiple Oligonucleotides", *Nucleic Acids Res.*, 18(24):7457–7458 (1990).*

*Pharmacia Catalog*, pp. 70–71 (1993 Edition).*

Piepersberg, "Pathway Engineering in Secondary Metabolite–Producing Actinomycetes", *Crit. Rev. Biotech.*, 14(3):251–285 (1994).*

Pompon et al., "Protein Engineering by cDNA Recombination in Yeasts: Shuffling of Mammalian Cytochrome P–450 Functions," *Gene*, 83(1):15–24 (1989).*

Prasher, "Using GFP to see the light", *TIG*, 11(8) (Aug. 1995).*

Rao et al., "Recombination and Polymerase Error Facilitate Restoration of Infectivity in Brome Mosaic Virus," *Journal of Virology*, 67(2):969–979 (1993).*

Rapley, "Enhancing PCR Amplification And Sequencing Using DNA–Binding Proteins", *Mol. Biotechnol.*, 2(3):295–298 (1994).*

Reidhaar–Olson et al., "Combinatorial Cassette Mutagenesis as a Probe of the Informational Content of Protein Sequences," *Science*, 241:53–57 (1988).*

Rice et al., "Random PCR mutagenesis screening of secreted proteins by direct expression in mammalian cells", *PNAS*, 89: 5467–5471 (Jun. 1992).*

Robles et al., "Hydropathy and Molar Volume Constraints on Combinatorial mutants of the Photosynthetic Reaction Center," *J. Mol. Biol.*, 232:242–252 (1993).*

Saiki et al., "Diagnosis of sickle Cell Anemia and β–Thalassemia with Enzymatically Amplified DNA and Nonradioactive Allele–Specific Oligonucleotide Probes," *New England J. of Medicine*, 319(9):537–541 (Sep. 1, 1988).*

Saiki et al., "analysis of enzymatically amplified β–globin and HLA–DQα DNA with allele–specific oligonucleotide probes," *Nature*, 324:163–166 (Nov. 13, 1986).*

Saiki et al., "Enzymatic Amplification of β–Globin Genomic Sequences and Restriction Site analysis for Diagnosis of Sickle Cell Anemia," *Science*, 230:1350–1354 (Dec. 20, 1985).*

Saiki et al., "Primer–Directed Enzymatic Amplification of DNA with a Thermostabl;e DNA Polymerase," *Science*, 239:487–491 (Jan. 20, 1988).*

Sambrook et al., *Molecular Cloning, A Laboratory Manual*, Cold Spring Laboratory Press, Cold Spring Harbor, New York (1989).*

Scharf et al., "Direct Cloning and Sequence Analysis of Enzymatically Amplified Genomic Sequences," *Science*, 233:1076–1078 (Sep. 1986).*

Scott et al., "Searching for Peptide Ligands with an Epitope Library," *Science*, 249:386–390 (Jul. 20, 1990).*

Sikorski et al., "In Vitro Mutagenesis and Planned Shuffling: From Cloned Gene to Mutant Yeast," *Methods in Enzymology*, 194:302–318 (1991).*

Simpson et al., "Two paradigms of metabolic engineering applied to amino acid biosynthesis", *Biochem. Soc. Transactions*, vol. 23 (1995).*

Smith et al., "Unwanted Mutations in PCR Mutagenesis: Avoiding the Predictable," *PCR Methods and Applications*, 2(3):253–257 (Feb. 1993).*

Steele et al., "Techniques for Selection of Industrially Important Microorganisms", *Ann. Rev. Microbiol.*, 45: 89–106 (1991).*

Stemmer, "Rapid Evolution of a Protein in Vitro by DNA Shuffling," *Nature*, 370:389–391 (1994).*

Stemmer, "DNA Shuffling by Random Fragmentation and Reassembly: In Vitro Recombination for Molecular Evolution" *Proc. Natl. Acad. Sci. USA*, 91(22):10747–10751 (1994).*

Stemmer et al., "Selection of an Active Single Chain FV Antibody from a Protein Linker Library Prepared by Enzymatic Inverse PCR," *Biotechniques*, 14(2):256–265 (1992).*

Stemmer, "Searching Sequence Space", *Biotechnology*, 13:549–553 (1995).*

Stemmer et al., "Single–Step Assembly Of A Gene And Entire Plasmid From Large Numbers Of Oligodeoxyribonucleotides", *Gene*, 164(1):49–53 (1995).*

Stemmer, "The Evolution of Molecular Computation", *Science*, 270(5241):1510 (1995).*

Stemmer, "Sexual PCR and Assembly PCR" *Encyclopedia Mol. Biol.*, VCH Publishers, New York, pp. 447–457 (1996).*

Stephanopoulos et al., "Metabolic engineering—methodologies and future prospects", *Trends Biotech.* 11: 392–396 (1993).*

Stephanopoulos, "Metabolic engineering", *Curr. Opin. Biotech.*, 5: 196–200 (1994).*

Villarreal et al., "A General Method of Polymerase–Chain–Reaction–Enabled Protein Domain Mutagenesis: Construction of a Human Protein S–Osteonectin Gene," *Analytical Biochem.*, 197:362–367 (1991).*

Wang et al., "Identification Of Glial Filament Protein And Vimentin In The Same Intermediate Filament System In Human Glioma Cells", *Proc. Natl. Acad. Sci. USA*, 81(7):2102–2106 (1984).*

Weber et al., "Formation of Genes Coding for Hybrid Proteins by Recombination Between Related, Cloned Genes in *E. coli*," *Nucleic Acids Research*, 11(16):5661–5669 (1983).*

Wehmeier, "New multifunctional *Escherichia coli–Streptomyces* shuttle vectors allowing blue–white screening on XGal plates", *Gene*, 165: 149–150 (1995).*

Weisberg et al., "Simultaneous Mutagenesis Of Multiple Sites: Application Of The Ligase Chain Reaction Using PCR Products Instead Of Oligonucleotides", *BioTechniques*, 15(1):68–76 (1993).*

Weissenhorn et al., "Chimerization of antibodies by isolation of rearranged genomic variable regions by the polymerase chain reaction," *Gene*, 106:273–277 (1991).*

Winter et al., "Making Antibodies By Phage Display Technology", *Ann. Rev. Immunol.*, 12:433–455 (1994).*

Yao et al., "Site–directed Mutagenesis of Herpesvirus Glycoprotein Phosphorylation Sites by Recombination Polymerase Chain Reaction," *PCR Methods and Applications*, 1(3):205–207 (Feb. 1992).*

Yolov et al., "Constructing DNA by polymerase recombination," *Nuc. Acids Res.*, 18(13):3983–3986 (1990).*

Yon et al., "Precise gene fusion by PCR," *Nuc. Acids Res.*, 17(12):4895 (1989).*

Youvan et al., "Recursive Ensemble Mutagenesis: A Combinatorial Optimization Technique for Protein Engineering," from Parallel Problem Solving from Nature, 2, Manner eds., pp. 401–410 (1992).*

Zhang et al., "Directed Evolution Of A Fucosidase From A Galactosidase by DNA Shuffling And Screening", *Proc. Natl. Acad. Sci. USA*, 94(9):4504–4509 (1997).*

Zhao et al., "Molecular Evolution by Staggered Extension Process (StEP) In Vitro Recombination", *Nature Biotech.*, 16:258–261 (1998).*

Zoller, M.J., "New recombinant DNA methodology for protein engineering," *Curr. Opin. Biotech.*, 3:348–354 (1992).*

Opposition Statement in matter of Australian Patent Application 703264 (Affymax Technologies NV), filed by Diversa Corporation on Sept. 23, 1999.* forward primers: P50F: 5'-GGCGGAGCTAGCTTCGTA-3' (SEQ. ID. NO: 21)
(mutagenic primer, underlined base is the mutagenized base at position 598)
P200F: 5'-GATGTGATGGCTCCTGGC-3' (SEQ. ID. NO: 22)

reverse primers: P80R: 5'-CAGAACACCGATTGAGTT-3' (SEQ. ID. NO: 23)
P250R: AGTGCTTTCTAAACGATC-3' (SEQ. ID. NO: 24)

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
        (A) LENGTH: 22 nucleotides
        (B) TYPE: nucleotide
        (C) STRANDEDNESS: single
        (D) TOPOLOGY: linear (ii) MOLECULE TYPE: oligonucleotide (xi) SEQUENCE DESCRIPTION: SEQ ID NO: 1:

CCG AGC GTT GCA TAT GTG AAA G                                          22

(2) INFORMATION FOR SEQ ID NO: 2:

(i) SEQUENCE CHARACTERISTICS:
        (A) LENGTH: 21 nucleotides
        (B) TYPE: nucleotide
        (C) STRANDEDNESS: single
        (D) TOPOLOGY: linear (ii) MOLECULE TYPE: oligonucleotide (xi) SEQUENCE DESCRIPTION: SEQ ID NO: 2:

CGA CTC TAG AGG ATC CGA TTC                                            21

(2) INFORMATION FOR SEQ ID NO: 3:

(i) SEQUENCE CHARACTERISTICS:
        (A) LENGTH: 21 nucleotides
        (B) TYPE: nucleotide
        (C) STRANDEDNESS: single
        (D) TOPOLOGY: linear (ii) MOLECULE TYPE: oligonucleotide (xi) SEQUENCE DESCRIPTION: SEQ ID NO: 3:

GAG CAC ATC AGA TCT ATT AAC                                            21

(2) INFORMATION FOR SEQ ID NO: 4:

(i) SEQUENCE CHARACTERISTICS:
        (A) LENGTH: 21 nucleotides
        (B) TYPE: nucleotide
        (C) STRANDEDNESS: single
        (D) TOPOLOGY: linear (ii) MOLECULE TYPE: oligonucleotide (xi) SEQUENCE DESCRIPTION: SEQ ID NO: 4:

GGA GTG GCT CAC AGT CGG TGG                                            21

(2) INFORMATION FOR SEQ ID NO: 5:

(i) SEQUENCE CHARACTERISTICS:
        (A) LENGTH: 21 nucleotides
        (B) TYPE: nucleotide
        (C) STRANDEDNESS: single
        (D) TOPOLOGY: linear (ii) MOLECULE TYPE: oligonucleotide (xi) SEQUENCE DESCRIPTION: SEQ ID NO: 5:

```
TTG AAC TAT CGG CTG GGG CGG                                          21

(2) INFORMATION FOR SEQ ID NO: 6:

(i) SEQUENCE CHARACTERISTICS:
          (A) LENGTH: 21 nucleotides
          (B) TYPE: nucleotide
          (C) STRANDEDNESS: single
          (D) TOPOLOGY: linear (ii) MOLECULE TYPE: oligonucleotide (xi) SEQUENCE DESCRIPTION: SEQ ID NO: 6:

TTA CTA GGG AAG CCG CTG GCA                                          21

(2) INFORMATION FOR SEQ ID NO: 7:

(i) SEQUENCE CHARACTERISTICS:
          (A) LENGTH: 21 nucleotides
          (B) TYPE: nucleotide
          (C) STRANDEDNESS: single
          (D) TOPOLOGY: linear (ii) MOLECULE TYPE: oligonucleotide (xi) SEQUENCE DESCRIPTION: SEQ ID NO: 7:

TCA GAG ATT ACG ATC GAA AAC                                          21

(2) INFORMATION FOR SEQ ID NO: 8:

(i) SEQUENCE CHARACTERISTICS:
          (A) LENGTH: 21 nucleotides
          (B) TYPE: nucleotide
          (C) STRANDEDNESS: single
          (D) TOPOLOGY: linear (ii) MOLECULE TYPE: oligonucleotide (xi) SEQUENCE DESCRIPTION: SEQ ID NO: 8:

GGA TTG TAT CGT GTG AGA AAG                                          21

(2) INFORMATION FOR SEQ ID NO: 9:

(i) SEQUENCE CHARACTERISTICS:
          (A) LENGTH: 21 nucleotides
          (B) TYPE: nucleotide
          (C) STRANDEDNESS: single
          (D) TOPOLOGY: linear (ii) MOLECULE TYPE: oligonucleotide (xi) SEQUENCE DESCRIPTION: SEQ ID NO: 9:

AAT GCC GGA AGC AGC CCC TTC                                          21

(2) INFORMATION FOR SEQ ID NO: 10:

(i) SEQUENCE CHARACTERISTICS:
          (A) LENGTH: 21 nucleotides
          (B) TYPE: nucleotide
          (C) STRANDEDNESS: single
          (D) TOPOLOGY: linear (ii) MOLECULE TYPE: oligonucleotide (xi) SEQUENCE DESCRIPTION: SEQ ID NO: 10:

CAC GAC AGG AAG ATT TTG ACT                                          21
```

(2) INFORMATION FOR SEQ ID NO: 11:

(i) SEQUENCE CHARACTERISTICS:
        (A) LENGTH: 20 nucleotides
        (B) TYPE: nucleotide
        (C) STRANDEDNESS: single
        (D) TOPOLOGY: linear (ii) MOLECULE TYPE: oligonucleotide (xi) SEQUENCE DESCRIPTION: SEQ ID NO: 11:

ACT TAA TCT AGA GGG TAT TA                    20

(2) INFORMATION FOR SEQ ID NO: 12:

(i) SEQUENCE CHARACTERISTICS:
        (A) LENGTH: 20 nucleotides
        (B) TYPE: nucleotide
        (C) STRANDEDNESS: single
        (D) TOPOLOGY: linear (ii) MOLECULE TYPE: oligonucleotide (xi) SEQUENCE DESCRIPTION: SEQ ID NO: 12:

AGC CTC GCG GGA TCC CCG GG                    20

(2) INFORMATION FOR SEQ ID NO: 13:

(i) SEQUENCE CHARACTERISTICS:
        (A) LENGTH: 28 nucleotides
        (B) TYPE: nucleotide
        (C) STRANDEDNESS: single
        (D) TOPOLOGY: linear (ii) MOLECULE TYPE: oligonucleotide (xi) SEQUENCE DESCRIPTION: SEQ ID NO: 13:

GGT AGA GCG AGT CTC GAG GGG GAG ATG C          28

(2) INFORMATION FOR SEQ ID NO: 14:

(i) SEQUENCE CHARACTERISTICS:
        (A) LENGTH: 22 nucleotides
        (B) TYPE: nucleotide
        (C) STRANDEDNESS: single
        (D) TOPOLOGY: linear (ii) MOLECULE TYPE: oligonucleotide (xi) SEQUENCE DESCRIPTION: SEQ ID NO: 14:

AGC CGG CGT GAC GTG GGT CAG C                22

(2) INFORMATION FOR SEQ ID NO: 15:

(i) SEQUENCE CHARACTERISTICS:
        (A) LENGTH: 22 nucleotides
        (B) TYPE: nucleotide
        (C) STRANDEDNESS: single
        (D) TOPOLOGY: linear (ii) MOLECULE TYPE: oligonucleotide (xi) SEQUENCE DESCRIPTION: SEQ ID NO: 15:

CCG AGC GTT GCA TAT GTG AA G                22

(2) INFORMATION FOR SEQ ID NO: 16:

(i) SEQUENCE CHARACTERISTICS:
        (A) LENGTH: 21 nucleotides (B) TYPE: nucleotide
       (C) STRANDEDNESS: single
       (D) TOPOLOGY: linear (ii) MOLECULE TYPE: oligonucleotide (xi) SEQUENCE DESCRIPTION: SEQ ID NO: 16:

CGA CTC TAG AGG ATC CGA TTC                                           21

(2) INFORMATION FOR SEQ ID NO: 17:

(i) SEQUENCE CHARACTERISTICS:
       (A) LENGTH: 22 nucleotides
       (B) TYPE: nucleotide
       (C) STRANDEDNESS: single
       (D) TOPOLOGY: linear (ii) MOLECULE TYPE: oligonucleotide (xi) SEQUENCE DESCRIPTION: SEQ ID NO: 17:

CGG TAC GCA TGT AGC CGG TAC G                                         22

(2) INFORMATION FOR SEQ ID NO: 18:

(i) SEQUENCE CHARACTERISTICS:
       (A) LENGTH: 22 nucleotides
       (B) TYPE: nucleotide
       (C) STRANDEDNESS: single
       (D) TOPOLOGY: linear (ii) MOLECULE TYPE: oligonucleotide (xi) SEQUENCE DESCRIPTION: SEQ ID NO: 18:

CGG TAC GAT TGC CGC CGG TAC G                                         22

(2) INFORMATION FOR SEQ ID NO: 19:

(i) SEQUENCE CHARACTERISTICS:
       (A) LENGTH: 22 nucleotides
       (B) TYPE: nucleotide
       (C) STRANDEDNESS: single
       (D) TOPOLOGY: linear (ii) MOLECULE TYPE: oligonucleotide (xi) SEQUENCE DESCRIPTION: SEQ ID NO: 19:

CCG AGC GTT GCA TAT GTG AAA G                                         22

(2) INFORMATION FOR SEQ ID NO: 20:

(i) SEQUENCE CHARACTERISTICS:
       (A) LENGTH: 21 nucleotides
       (B) TYPE: nucleotide
       (C) STRANDEDNESS: single
       (D) TOPOLOGY: linear (ii) MOLECULE TYPE: oligonucleotide (xi) SEQUENCE DESCRIPTION: SEQ ID NO: 20:

CGA CTC TAG AGG ATC CGA TTC                                           21

(2) INFORMATION FOR SEQ ID NO: 21:

(i) SEQUENCE CHARACTERISTICS:
       (A) LENGTH: 18 nucleotides
       (B) TYPE: nucleotide
       (C) STRANDEDNESS: single
       (D) TOPOLOGY: linear -continued (ii) MOLECULE TYPE: oligonucleotide (xi) SEQUENCE DESCRIPTION: SEQ ID NO: 21:

GGC GGA GCT AGC TTC GTA                                          18

(2) INFORMATION FOR SEQ ID NO: 22:

(i) SEQUENCE CHARACTERISTICS:
        (A) LENGTH: 18 nucleotides
        (B) TYPE: nucleotide
        (C) STRANDEDNESS: single
        (D) TOPOLOGY: linear (ii) MOLECULE TYPE: oligonucleotide (xi) SEQUENCE DESCRIPTION: SEQ ID NO: 22:

GAT GTG ATG GCT CCT GGC                                          18

(2) INFORMATION FOR SEQ ID NO: 23:

(i) SEQUENCE CHARACTERISTICS:
        (A) LENGTH: 18 nucleotides
        (B) TYPE: nucleotide
        (C) STRANDEDNESS: single
        (D) TOPOLOGY: linear (ii) MOLECULE TYPE: oligonucleotide (xi) SEQUENCE DESCRIPTION: SEQ ID NO: 23:

CAG AAC ACC GAT TGA GTT                                          18

(2) INFORMATION FOR SEQ ID NO: 24:

(i) SEQUENCE CHARACTERISTICS:
        (A) LENGTH: 18 nucleotides
        (B) TYPE: nucleotide
        (C) STRANDEDNESS: single
        (D) TOPOLOGY: linear (ii) MOLECULE TYPE: oligonucleotide (xi) SEQUENCE DESCRIPTION: SEQ ID NO: 24:

AGT GCT TTC TAA ACG ATC                                          18

(2) INFORMATION FOR SEQ ID NO: 25:

(i) SEQUENCE CHARACTERISTICS:
        (A) LENGTH: 4 amino acids
        (B) TYPE: amino acid
        (C) TOPOLOGY: linear (ii) MOLECULE TYPE: peptide (xi) SEQUENCE DESCRIPTION: SEQ ID NO: 25:

Ala Ala Pro Phe

RECOMBINATION OF POLYNUCLEOTIDE SEQUENCES USING RANDOM OR DEFINED PRIMERS

This application is a divisional of U.S. Ser. No. 08/905,359, filed Aug. 4, 1997, which claims the benefit of U.S. provisional No. 60/041,666, filed Mar. 25, 1997, and U.S. provisional No. 60/045,211, filed Apr. 30, 1997, and U.S. provisional No. 60/046,256, filed May 12, 1997, and is a continuation-in-part of Ser. No. 08/905,058, filed Aug. 1, 1997, now abandoned, the disclosures of which are incorporated by reference in their entirety for all purposes.

The U.S. Government has certain rights in this invention pursuant to Grant No. DE-FG02-93-CH10578 awarded by the Department of Energy and Grant No. N00014-96-1-0340 awarded by the Office of Naval Research.

BACKGROUND OF THE INVENTION

1. Field of the Invention

The present invention relates generally to in vitro methods for mutagenesis and recombination of polynucleotide sequences. More particularly, the present invention involves a simple and efficient method for in vitro mutagenesis and recombination of polynucleotide sequences based on polymerase-catalyzed extension of primer oligonucleotides, followed by gene assembly and optional gene amplification.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography.

Proteins are engineered with the goal of improving their performance for practical applications. Desirable properties depend on the application of interest and may include tighter binding to a receptor, high catalytic activity, high stability, the ability to accept a wider (or narrower) range of substrates, or the ability to function in nonnatural environments such as organic solvents. A variety of approaches, including 'rational' design and random mutagenesis methods, have been successfully used to optimize protein functions (1). The choice of approach for a given optimization problem will depend upon the degree of understanding of the relationships between sequence, structure and function. The rational redesign of an enzyme catalytic site, for example, often requires extensive knowledge of the enzyme structure, the structures of its complexes with various ligands and analogs of reaction intermediates and details of the catalytic mechanism. Such information is available only for a very few well-studied systems; little is known about the vast majority of potentially interesting enzymes. Identifying the amino acids responsible for existing protein functions and those which might give rise to new functions remains an often-overwhelming challenge. This, together with the growing appreciation that many protein functions are not confined to a small number of amino acids, but are affected by residues far from active sites, has prompted a growing number of groups to turn to random mutagenesis, or 'directed' evolution, to engineer novel proteins (1).

Various optimization procedures such as genetic algorithms (2,3) and evolutionary strategies (4,5) have been inspired by natural evolution. These procedures employ mutation, which makes small random changes in members of the population, as well as crossover, which combines properties of different individuals, to achieve a specific optimization goal. There also exist strong interplays between mutation and crossover, as shown by computer simulations of different optimization problems (6–9). Developing efficient and practical experimental techniques to mimic these key processes is a scientific challenge. The application of such techniques should allow one, for example, to explore and optimize the functions of biological molecules such as proteins and nucleic acids, in vivo or even completely free from the constraints of a living system (10,11).

Directed evolution, inspired by natural evolution, involves the generation and selection or screening of a pool of mutated molecules which has sufficient diversity for a molecule encoding a protein with altered or enhanced function to be present therein. It generally begins with creation of a library of mutated genes. Gene products which show improvement with respect to the desired property or set of properties are identified by selection or screening. The gene(s) encoding those products can be subjected to further cycles of the process in order to accumulate beneficial mutations. This evolution can involve few or many generations, depending on how far one wishes to progress and the effects of mutations typically observed in each generation. Such approaches have been used to create novel functional nucleic acids (12), peptides and other small molecules (12), antibodies (12), as well as enzymes and other proteins (13,14,16). Directed evolution requires little specific knowledge about the product itself, only a means to evaluate the function to be optimized. These procedures are even fairly tolerant to inaccuracies and noise in the function evaluation (15).

The diversity of genes for directed evolution can be created by introducing new point mutations using a variety of methods, including mutagenic PCR (15) or combinatorial cassette mutagenesis (16). The ability to recombine genes, however, can add an important dimension to the evolutionary process, as evidenced by its key role in natural evolution. Homologous recombination is an important natural process in which organisms exchange genetic information between related genes, increasing the accessible genetic diversity within a species. While introducing potentially powerful adaptive and diversification competencies into their hosts, such pathways also operate at very low efficiencies, often eliciting insignificant changes in pathway structure or function, even after tens of generations. Thus, while such mechanisms prove beneficial to host organisms/species over geological time spans, in vivo recombination methods represent cumbersome, if not unusable, combinatorial processes for tailoring the performance of enzymes or other proteins not strongly linked to the organism's intermediary metabolism and survival.

Several groups have recognized the utility of gene recombination in directed evolution. Methods for in vivo recombination of genes are disclosed, for example, in published PCT application WO 97/07205 and U.S. Pat. No. 5,093,257. As discussed above, these in vivo methods are cumbersome and poorly optimized for rapid evolution of function. Stemmer has disclosed a method for in vitro recombination of related DNA sequences in which the parental sequences are cut into fragments, generally using an enzyme such as DNase I, and are reassembled (17,18,19). The non-random DNA fragmentation associated with DNase I and other endonucleases, however, introduces bias into the recombination and limits the recombination diversity. Furthermore, this method is limited to recombination of double-stranded polynucleotides and cannot be used on single-stranded templates. Further, this method does not work well with certain combinations of genes and primers. It is not efficient for recombination of short sequences (less than 200 nucleotides (nts)), for example. Finally, it is quite laborious, requiring several steps. Alternative, convenient methods for creating novel genes by point mutagenesis and recombination in vitro are needed.

SUMMARY OF THE INVENTION

The present invention provides a new and significantly improved approach to creating novel polynucleotide sequences by point mutation and recombination in vitro of a set of parental sequences (the templates). The novel polynucleotide sequences can be useful in themselves (for example, for DNA-based computing), or they can be expressed in recombinant organisms for directed evolution of the gene products. One embodiment of the invention involves priming the template gene(s) with random-sequence oligonucleotides to generate a pool of short DNA fragments. Under appropriate reaction conditions, these short DNA fragments can prime one another based on complementarity and thus can be reassembled to form full-length genes by repeated thermocycling in the presence of thermostable DNA polymerase. These reassembled genes, which contain point mutations as well as novel combinations of sequences from different parental genes, can be further amplified by conventional PCR and cloned into a proper vector for expression of the encoded proteins. Screening or selection of the gene products leads to new variants with improved or even novel functions. These variants can be used as they are, or they can serve as new starting points for further cycles of mutagenesis and recombination.

A second embodiment of the invention involves priming the template gene(s) with a set of primer oligonucleotides of defined sequence or defined sequence exhibiting limited randomness to generate a pool of short DNA fragments, which are then reassembled as described above into full length genes.

A third embodiment of the invention involves a novel process we term the 'staggered extension' process, or StEP. Instead of reassembling the pool of fragments created by the extended primers, full-length genes are assembled directly in the presence of the template(s). The StEP consists of repeated cycles of denaturation followed by extremely abbreviated annealing/extension steps. In each cycle the extended fragments can anneal to different templates based on complementarity and extend a little further to create "recombinant cassettes." Due to this template switching, most of the polynucleotides contain sequences from different parental genes (i.e. are novel recombinants). This process is repeated until full-length genes form. It can be followed by an optional gene amplification step.

The different embodiments of the invention provide features and advantages for different applications. In the most preferred embodiment, one or more defined primers or defined primers exhibiting limited randomness which correspond to or flank the 5' and 3' ends of the template polynucleotides are used with StEP to generate gene fragments which grow into the novel full-length sequences. This simple method requires no knowledge of the template sequence(s).

In another preferred embodiment, multiple defined primers or defined primers exhibiting limited randomness are used to generate short gene fragments which are reassembled into full-length genes. Using multiple defined primers allows the user to bias in vitro recombination frequency.

If sequence information is available, primers can be designed to generate overlapping recombination cassettes which increase the frequency of recombination at particular locations. Among other features, this method introduces the flexibility to take advantage of available structural and functional information as well as information accumulated through previous generations of mutagenesis and selection (or screening).

In addition to recombination, the different embodiments of the primer-based recombination process will generate point mutations. It is desirable to know and be able to control this point mutation rate, which can be done by manipulating the conditions of DNA synthesis and gene reassembly. Using the defined-primer approach, specific point mutations can also be directed to specific positions in the sequence through the use of mutagenic primers.

The various primer-based recombination methods in accordance with this invention have been shown to enhance the activity of *Actinoplanes utahensis* ECB deacylase over a broad range of pH values and in the presence of organic solvent and to improve the thermostability of *Bacillus subtilis* subtilisin E. DNA sequencing confirms the role of point mutation and recombination in the generation of novel sequences. These protocols have been found to be both simple and reliable.

The above discussed and many other features and attendant advantages will become better understood by reference to the following detailed description when taken in conjunction with the accompanying drawings.

DETAILED DESCRIPTION OF THE INVENTION

Figure 1:
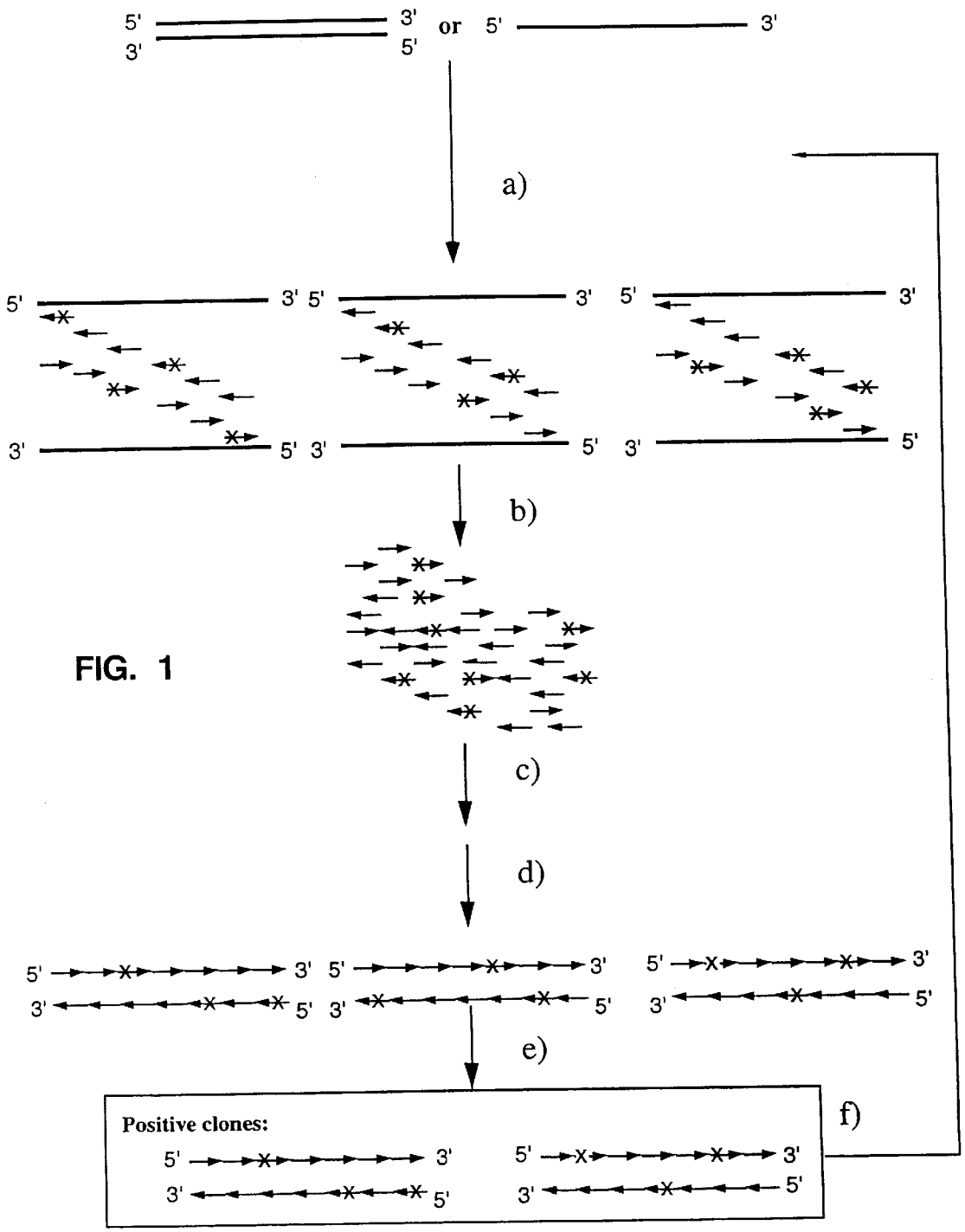
FIG. 1 depicts recombination in accordance with the present invention using random-sequence primers and gene reassembly. The steps shown are: a) Synthesis of single-stranded DNA fragments using mesophilic or thermophilic polymerase with random-sequence oligonucleotides as primers (primers not shown); b) Removal of templates; c) Reassembly with thermophilic DNA polymerase; d) Amplification with thermostable polymerase(s); e) Cloning and Screening (optional); and f) Repeat the process with selected gene(s) (optional).

In one preferred embodiment of the present invention, a set of primers with all possible nucleotide sequence combinations ($dp(N)_L$ where L=primer length) is used for the primer-based recombination. It has been known for years that oligodeoxynucleotides of different lengths can serve as primers for initiation of DNA synthesis on single-stranded templates by the Klenow fragment of *E.coli* polymerase I (21). Although they are smaller than the size of a normal PCR primer (i.e. less than 13 bases), oligomers as short as hexanucleotides can adequately prime the reaction and are frequently used in labeling reactions (22). The use of random primers to create a pool of gene fragments followed by gene reassembly in accordance with the invention is shown in FIG. 1. The steps include generation of diverse "breeding blocks" from the single-stranded polynucleotide templates through random priming, reassembly of the full-length DNA from the generated short, nascent DNA fragments by thermocycling in the presence of DNA polymerase and nucleotides, and amplification of the desired genes from the reassembled products by conventional PCR for further cloning and screening. This procedure introduces new mutations mainly at the priming step but also during other steps. These new mutations and the mutations already present in the template sequences are recombined during reassembly to create a library of novel DNA sequences. The process can be repeated on the selected sequences, if desired.

To carry out the random priming procedure, the template (s) can be single- or denatured double-stranded polynucleotide(s) in linear or closed circular form. The templates can be mixed in equimolar amounts, or in amounts weighted, for example, by their functional attributes. Since, at least in some cases, the template genes are cloned in vectors into which no additional mutations should be introduced, they are usually first cleaved with restriction endonuclease(s) and purified from the vectors. The resulting linear DNA molecules are denatured by boiling, annealed to random-sequence oligodeoxynucleotides and incubated with DNA polymerase in the presence of an appropriate amount of dNTPs. Hexanucleotide primers are preferred, although longer random primers (up to 24 bases) may also be used, depending on the DNA polymerase and conditioning used during random priming synthesis. Thus the oligonucleotides prime the DNA of interest at various positions along the entire target region and are extended to generate short DNA fragments complementary to each strand of the template DNA. Due to events such as base misincorporations and mispriming, these short DNA fragments also contain point mutations. Under routinely established reaction conditions, the short DNA fragments can prime one another based on homology and be reassembled into full-length genes by repeated thermocycling in the presence of thermostable DNA polymerase. The resulting full-length genes will have diverse sequences, most of which, however, still resemble that of the original template DNA. These sequences can be further amplified by a conventional PCR and cloned into a vector for expression. Screening or selection of the expressed mutants should lead to variants with improved or even new specific functions. These variants can be immediately used as partial solutions to a practical problem, or they can serve as new starting points for further cycles of directed evolution.

Compared to other techniques used for protein optimization, such as combinatorial cassette and oligonucleotide-directed mutagenesis (24,25,26), error-prone PCR (27, 28), or DNA shuffling (17,18,19), some of the advantages of the random-primer based procedure for in vitro protein evolution are summarized as follows:

1. The template(s) used for random priming synthesis may be either single- or double-stranded polynucleotides. In contrast, error-prone PCR and the DNA shuffling method for recombination (17,18,19) necessarily employ only double-stranded polynucleotides. Using the technique described here, mutations and/or crossovers can be introduced at the DNA level by using different DNA-dependent DNA polymerases, or even directly from mRNA by using different RNA-dependent DNA polymerases. Recombination can be performed using single-stranded DNA templates.
2. In contrast to the DNA shuffling procedure, which requires fragmentation of the double-stranded DNA template (generally done with DNAse I) to generate random fragments, the technique described here employs random priming synthesis to obtain DNA fragments of controllable size as "breeding blocks" for further reassembly (FIG. 1). One immediate advantage is that two sources of nuclease activity (DNase I and 5'-3' exonuclease) are eliminated, and this allows easier control over the size of the final reassembly and amplification gene fragments.
3. Since the random primers are a population of synthetic oligonucleotides that contain all four bases in every position, they are uniform in their length and lack a sequence bias. The sequence heterogeneity allows them to form hybrids with the template DNA strands at many positions, so that every nucleotide of the template (except, perhaps, those at the extreme 5' terminus) should be copied at a similar frequency into products. In this way, both mutations and crossover may happen more randomly than, for example, with error-prone PCR or DNA shuffling.
4. The random-primed DNA synthesis is based on the hybridization of a mixture of hexanucleotides to the DNA templates, and the complementary strands are synthesized from the 3'-OH termini at the random hexanucleotide primer using polymerase and the four deoxynucleotide triphosphates. Thus the reaction is independent of the length of the DNA template. DNA fragments of 200 bases length can be primed equally well as linearized plasmid or λ DNA (29). This is particularly useful for engineering peptides, for example.
5. Since DNase I is an endonuclease that hydrolyzes double-stranded DNA preferentially at sites adjacent to pyrimidine nucleotides, its use in DNA shuffling may result in bias (particularly for genes with high G+C or high A+T content) at the step of template gene digestion. Effects of this potential bias on the overall mutation rate and recombination frequency may be avoided by using the random-priming approach. Bias in random priming due to preferential hybridization to GC-rich regions of the template DNA could be overcome by increasing the A and T content in the random oligonucleotide library.

An important part of practicing the present invention is controlling the average size of the nascent, single-strand DNA synthesized during the random priming process. This step has been studied in detail by others. Hodgson and Fisk (30) found that the average size of the synthesized single-strand DNA is an inverse function of primer concentration: length=$k/\sqrt{\ln Pc}$, where $P_c$ is the primer concentration. The inverse relationship between primer concentration and output DNA fragment size may be due to steric hindrance. Based on this guideline, proper conditions for random-priming synthesis can be readily set for individual genes of different lengths.

Since dozens of polymerases are currently available, synthesis of the short, nascent DNA fragments can be achieved in a variety of fashions. For example, bacteriophage T4 DNA polymerase (23) or T7 sequenase version 2.0 DNA polymerase (31,32) can be used for the random priming synthesis.

For single-stranded polynucleotide templates (particularly for RNA templates), a reverse transcriptase is preferred for random-priming synthesis. Since this enzyme lacks 3'→5' exonuclease activity, it is rather prone to error. In the presence of high concentrations of dNTPs and $Mn^{2+}$, about 1 base in every 500 is misincorporated (29).

By modifying the reaction conditions, the PCR can be adjusted for the random priming synthesis using thermostable polymerase for the short, nascent DNA fragments. An important consideration is to identify by routine experimentation the reaction conditions which ensure that the short random primers can anneal to the templates and give sufficient DNA amplification at higher temperatures. We have found that random primers as short as $dp(N)_{12}$ can be used with PCR to generate the extended primers. Adapting the PCR to the random priming synthesis provides a convenient method to make short, nascent DNA fragments and makes this random priming recombination technique very robust.

In many evolution scenarios, recombination should be conducted between oligonucleotide sequences for which sequence information is available for at least some of the template sequences. In such scenarios, it is often possible to define and synthesize a series of primers which are interspersed between the various mutations. When defined primers are used, they can be between 6 and 100 bases long. In accordance with the present invention, it was discovered that by allowing these defined primers to initiate a series of overlapping primer extension reactions (which may be facilitated by thermocycling), it is possible to generate recombination cassettes each containing one or more of the accumulated mutations, allelic or isotypic differences between templates. Using the defined primers in such a way that overlapping extension products are generated in the DNA polymerization reactions, exhaustion of available primer leads to the progressive cross-hybridization of primer extended products until complete gene products are generated. The repeated rounds of annealing, extension and denaturation assure recombination of each overlapping cassette with every other.

Figure 2:
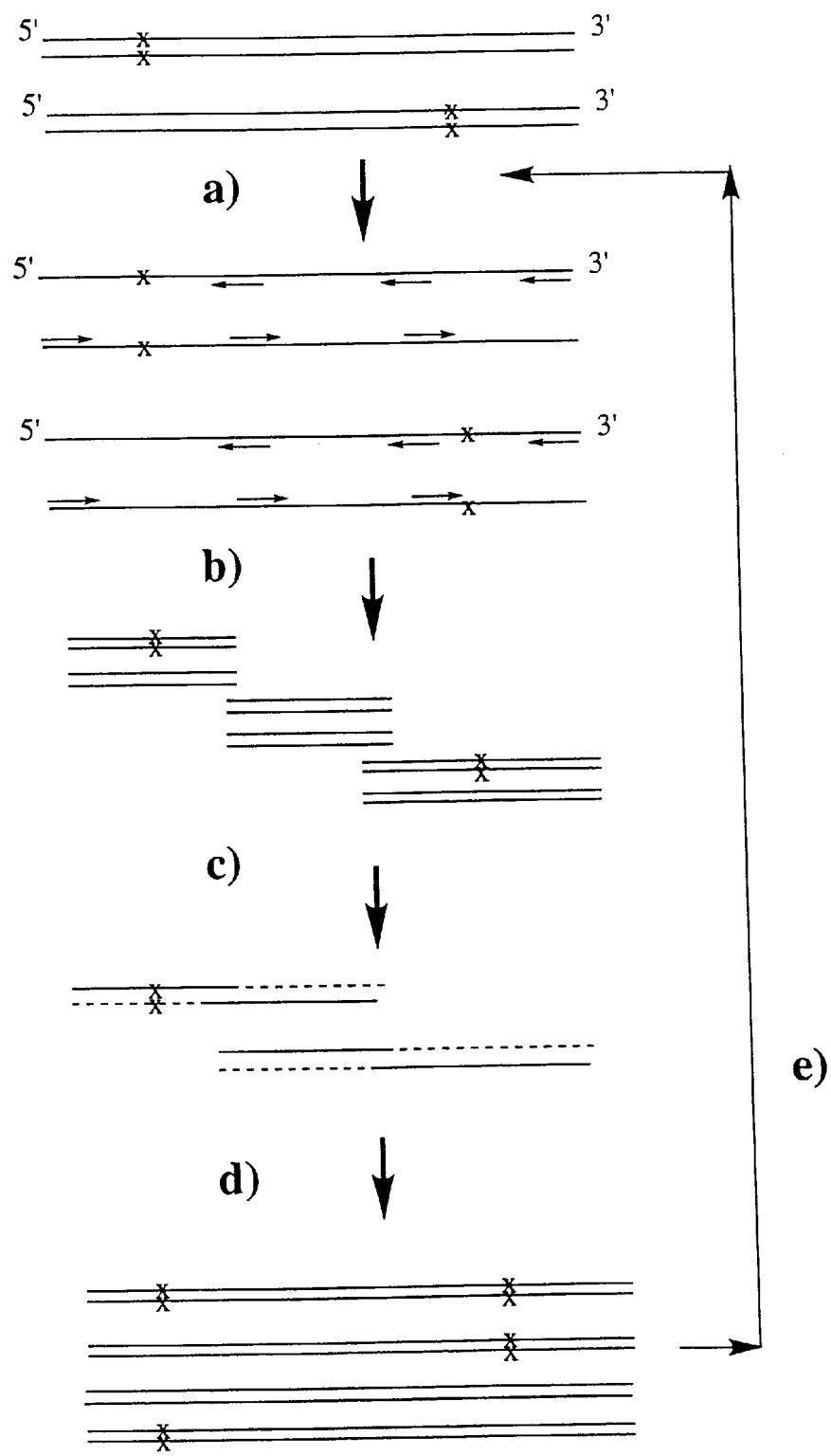
FIG. 2 depicts recombination in accordance with the present invention using defined primers. The method is illustrated for the recombination of two genes, where x=mutation. The steps diagrammed are: a) The genes are primed with defined primers in PCR reactions that can be done separately (2 primers per reaction) or combined (multiple primers per reaction); c) Initial products are formed until defined primers are exhausted. Template is removed (optional); d) Initial fragments prime and extend themselves in further cycles of PCR with no addition of external primers. Assembly continues until full-length genes are formed; e) (optional) Full-length genes are amplified in a PCR reaction with external primers; f) (optional) Repeat the process with selected gene(s).

A preferred embodiment of the present invention involves methods in which a set of defined oligonucleotide primers is used to prime DNA synthesis. FIG. 2 illustrates an exemplary version of the present invention in which defined primers are used. Careful design and positioning of oligonucleotide primers facilitates the generation of non-random extended recombination primers and is used to determine the major recombination (co-segregation) events along the length of homologous templates.

Figure 3:
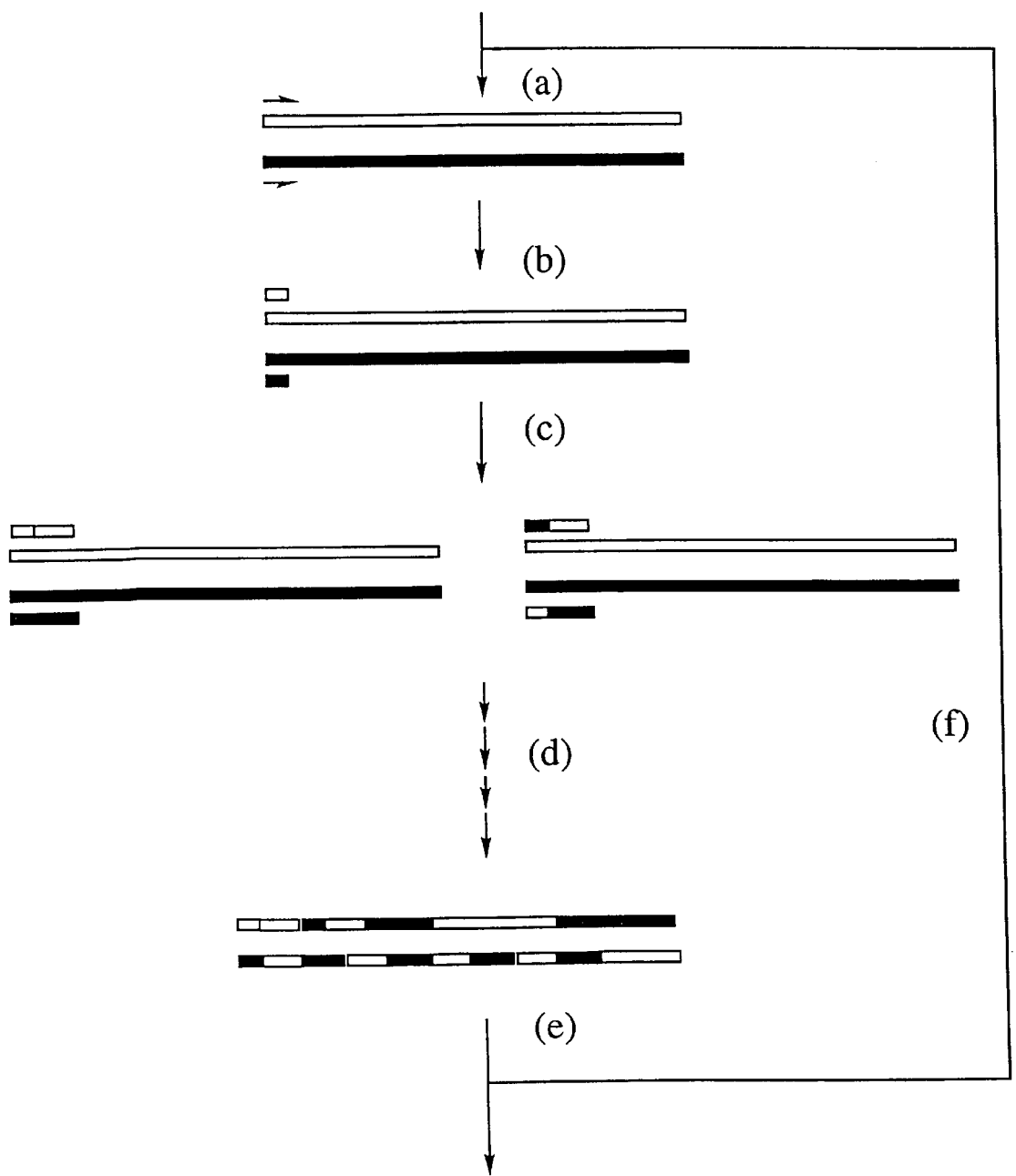
FIG. 3 depicts recombination in accordance with the present invention using two defined flanking primers and StEP. Only one primer and two single strands from two templates are shown here to illustrate the recombination process. The outlined steps are: a) After denaturation, template genes are primed with one defined primer; b) Short fragments are produced by primer extension for a short time; c) In the next cycle of StEP, fragments are randomly primed to the templates and extended further; d) Denaturation and annealing/extension is repeated until full-length genes are made (visible on an agarose gel); e) Full-length genes are purified, or amplified in a PCR reaction with external primers (optional); f) (optional) Repeat the process with selected gene(s).

Another embodiment of the present invention is an alternative approach to primer-based gene assembly and recombination in the presence of template. Thus, as illustrated in FIG. 3, the present invention includes recombination in which enzyme-catalyzed DNA polymerization is allowed to proceed only briefly (by limiting the time and lowering the temperature of the extension step) prior to denaturation. Denaturation is followed by random annealing of the extended fragments to template sequences and continued partial extension. This process is repeated multiple times, depending on the concentration of primer and template, until full length sequences are made. This process is called staggered extension, or StEP. Although random primers can also be used for StEP, gene synthesis is not nearly as efficient as with defined primers. Thus defined primers are preferred.

In this method, a brief annealing/extension step(s) is used to generate the partially extended primer. A typical annealing/extension step is done under conditions which allow high fidelity primer annealing ($T_{annealing}$ greater than $T_m^{-25}$), but limit the polymerization/extension to no more than a few seconds (or an average extension to less than 300 nts). Minimum extensions are preferably on the order of 20–50 nts. It has been demonstrated that thermostable DNA polymerases typically exhibit maximal polymerization rates of 100–150 nucleotides/second/enzyme molecule at optimal temperatures, but follow approximate Arrhenius kinetics at temperatures approaching the optimum temperature ($T_{opt}$). Thus, at a temperature of 55° C., a thermostable polymerase exhibits only 20–25% of the steady state polymerization rate that it exhibits at 72° C. ($T_{opt}$), or 24 nts/second (40). At 37° C. and 22° C., Taq polymerase is reported to have extension activities of 1.5 and 0.25 nts/second, respectively (24). Both time and temperature can be routinely altered based on the desired recombination events and knowledge of basic polymerase kinetics and biochemistry.

The progress of the staggered extension process is monitored by removing aliquots from the reaction tube at various time points in the primer extension and separating DNA fragments by agarose gel electrophoresis. Evidence of effective primer extension is seen from the appearance of a low molecular weight 'smear' early in the process which increases in molecular weight with increasing cycle number.

Unlike the gene amplification process (which generates new DNA exponentially), StEP generates new DNA fragments in an additive manner in its early cycles which contain DNA segments corresponding to the different template genes. Under non-amplifying conditions, 20 cycles of StEP generates a maximal molar yield of DNA of approximately 40 times the initial template concentration. In comparison, the idealized polymerase chain reaction process for gene amplification is multiplicative throughout, giving a maximal molar yield of approximately $1 \times 10^6$-fold through the same number of steps. In practice, the difference between the two processes can be observed by PCR, giving a clear 'band' after only a few (less than 10) cycles when starting with template at concentrations of less than 1 ng/ul and primers at 10–500-fold excess (vs. $10^6$-fold excess typical of gene amplification). Under similar reaction conditions, the StEP would be expected to give a less visible 'smear', which increases in molecular weight with increasing number of cycles. When significant numbers of primer extended DNA molecules begin to reach sizes of greater than ½ the length of the full length gene, a rapid jump in molecular weight occurs, as half-extended forward and reverse strands begin to cross-hybridize to generate fragments nearly 2 times the size of those encountered to that point in the process. At this point, consolidation of the smear into a discrete band of the appropriate molecular weight can occur rapidly by either continuing to subject the DNA to StEP, or altering the thermocycle to allow complete extension of the primed DNA to drive exponential gene amplification.

Following gene assembly (and, if necessary, conversion to double stranded form) recombined genes are amplified (optional), digested with suitable restriction enzymes and ligated into expression vectors for screening of the expressed gene products. The process can be repeated if desired, in order to accumulate sequence changes leading to the evolution of desired functions.

The staggered extension and homologous gene assembly process (StEP) represents a powerful, flexible method for recombining similar genes in a random or biased fashion. The process can be used to concentrate recombination within or away from specific regions of a known series of sequences by controlling placement of primers and the time allowed for annealing/extension steps. It can also be used to recombine specific cassettes of homologous genetic information generated separately or within a single reaction. The method is also applicable to recombining genes for which no sequence information is available but for which functional 5' and 3' amplification primers can be prepared. Unlike other recombination methods, the staggered extension process can be run in a single tube using conventional procedures without complex separation or purification steps.

Some of the advantages of the defined-primer embodiments of the present invention are summarized as follows:
1. The StEP method does not require separation of parent molecules from assembled products.
2. Defined primers can be used to bias the location of recombination events.
3. StEP allows the recombination frequency to be adjusted by varying extension times.
4. The recombination process can be carried out in a single tube.
5. The process can be carried out on single-stranded or double-stranded polynucleotides.
6. The process avoids the bias introduced by DNase I or other endonucleases.
7. Universal primers can be used.
8. Defined primers exhibiting limited randomness can be used to increase the frequency of mutation at selected areas of the gene.

As will be appreciated by those skilled in the art, several embodiments of the present invention are possible. Exemplary embodiments include:
1. Recombination and point mutation of related genes using only defined flanking primers and staggered extension.
2. Recombination and mutation of related genes using flanking primers and a series of internal primers at low enough concentration that exhaustion of the primers will occur over the course of the thermocycling, forcing the overlapping gene fragments to cross-hybridize and extend until recombined synthetic genes are formed.
3. Recombination and mutation of genes using random-sequence primers at high concentration to generate a pool of short DNA fragments which are reassembled to form new genes.
4. Recombination and mutation of genes using a set of defined primers to generate a pool of DNA fragments which are reassembled to form new genes.
5. Recombination and mutation of single-stranded polynucleotides using one or more defined primers and staggered extension to form new genes.
6. Recombination using defined primers with limited randomness at more than 30% or more than 60% of the nucleotide positions within the primer.

Examples of practice showing use of the primer-based recombination method are as follows.

EXAMPLE 1

Use of Defined Flanking Primers and Staggered Extension to Recombine and Enhance the Thermostability of Subtilisin E This example shows how the defined primer recombination method can be used to enhance the thermostability of subtilisin E by recombination of two genes known to encode subtilisin E variants with thermostabilities exceeding that of wild-type subtilisin E. This example demonstrates the general method outlined in FIG. 3 utilizing only two primers corresponding to the 5' and 3' ends of the templates.

As outlined in FIG. 3, extended recombination primers are first generated by the staggered extension process (StEP), which consists of repeated cycles of denaturation followed by extremely abbreviated annealing/extension step (s). The extended fragments are reassembled into full-length genes by thermocycling-assisted homologous gene assembly in the presence of a DNA polymerase, followed by an optional gene amplification step.

Two thermostable subtilisin E mutants R1 and R2 were used to test the defined primer based recombination technique using staggered extension. The positions at which these two genes differ from one another are shown in Table 1. Among the ten nucleotide positions that differ in R1 and R2, only those mutations leading to amino acid substitutions Asn 181-Asp (N181D) and Asn 218-Ser (N218S) confer thermostability. The remaining mutations are neutral with respect to their effects on thermostability (33). The half-lives at 65° C. of the single variants N181D and N218S are approximately 3-fold and 2-fold greater than that of wild type subtilisin E, respectively, and their melting temperatures, $T_m$, are 3.7° C. and 3.2° C. higher than that of wild type enzyme, respectively. Random recombination events that yield sequences containing both these functional mutations will give rise to enzymes whose half lives at 65° C. are approximately 8-fold greater than that of wild type subtilisin E, provided no new deleterious mutations are introduced into these genes during the recombination process. Furthermore, the overall point mutagenesis rate associated with the recombination process can be estimated from the catalytic activity profile of a small sampling of the recombined variant library. If the point mutagenesis rate is zero, 25% of the population should exhibit wild type-like activity, 25% of the population should have double mutant (N181D+N218S)-like activity and the remaining 50% should have single mutant (N181D or N218S)-like activity. Finite point mutagenesis increases the fraction of the library that encodes enzymes with wild-type like (or lower) activity. This fraction can be used to estimate the point mutagenesis rate.

TABLE 1

DNA and amino acid substitutions in thermostable subtilisin E mutants R1 and R2.

| Gene | Base | Base Substitution | Position in codon | Amino acid | Amino acid substitution |
|---|---|---|---|---|---|
| R1 | 780 | A→G | 2 | 109 | Asn→Ser |
|  | 1107 | A→G | 2 | 218 | Asn→Ser |
|  | 1141 | A→T | 3 | 229 | synonymous |
|  | 1153 | A→G | 3 | 233 | synonymous |
| R2 | 484 | A→G | 3 | 10 | synonymous |
|  | 520 | A→T | 3 | 22 | synonymous |
|  | 598 | A→G | 3 | 48 | synonymous |
|  | 731 | G→A | 1 | 93 | Val→Ile |

TABLE 1-continued

DNA and amino acid substitutions in thermostable subtilisin E mutants R1 and R2.

| Gene | Base | Base Substitution | Position in codon | Amino acid | Amino acid substitution |
|---|---|---|---|---|---|
|  | 745 | T→C | 3 | 97 | synonymous |
|  | 780 | A→G | 2 | 109 | Asn→Ser |
|  | 995 | A→G | 1 | 181 | Asn→Asp |
|  | 1189 | A→G | 3 | 245 | synonymous |

Mutations listed are relative to wild type subtilisin E with base substitution at 780 in common.

Materials and Methods
Procedure for Defined Primer Based Recombination Using Two Flanking Primers Two defined primers, P5N (5'-CCGAG CGTTG CATAT GTGGA AG-3' (SEQ. ID. NO: 1), underlined sequence is NdeI restriction site) and P3B (5'-CGACT CTAGA GGATC CGATT C-3' (SEQ. ID. NO: 2), underlined sequence is BamHI restriction site), corresponding to 5' and 3' flanking primers, respectively, were used for recombination. Conditions (100 ul final volume): 0.15 pmol plasmid DNA containing genes R1 and R2 (mixed at 1:1) were used as template, 15 pmol of each flanking primer, 1 times Taq buffer, 0.2 mM of each dNTP, 1.5 mM $MgCl_2$ and 0.25 U Taq polymerase. Program: 5 minutes of 95° C., 80 cycles of 30 seconds 94° C., 5 seconds 55° C. The product of correct size (approximately 1 kb) was cut from an 0.8% agarose gel after electrophoresis and purified using QIAEX II gel extraction kit. This purified product was digested with NdeI and BamHI and subcloned into pBE3 shuttle vector. This gene library was amplified in *E. coli* HB101 and transferred into *B. subtilis* DB428 competent cells for expression and screening, as described elsewhere (35).

DNA Sequencing

Genes were purified using QIAprep spin plasmid miniprep kit to obtain sequencing quality DNA. Sequencing was done on an ABI 373 DNA Sequencing System using the Dye Terminator Cycle Sequencing kit (Perkin-Elmer, Branchburg, N.J.).

Results

The progress of the staggered extension was monitored by removing aliquots (10 ul) from the reaction tube at various time points in the primer extension process and separating DNA fragments by agarose gel electrophoresis. Gel electrophoresis of primer extension reactions revealed that annealing/extension reactions of 5 seconds at 55° C. resulted in the occurrence of a smear approaching 100 bp (after 20 cycles), 400 bp (after 40 cycles), 800 bp (after 60 cycles) and finally a strong approximately 1 kb band within this smear. This band (mixture of reassembled products) was gel purified, digested with restriction enzyme BamHI and NdeI, and ligated with vector generated by BamHI-NdeI digestion of the *E. coli*/*B. subtilis* pBE3 shuttle vector. This gene library was amplified in *E. coli* HB101 and transferred into *B. subtlis* DB428 competent cells for expression and screening (35).

The thermostability of enzyme variants was determined in the 96-well plate format described previously (33). About 200 clones were screened, and approximately 25% retained subtilisin activity. Among these active clones, the frequency of the double mutant-like phenotype (high thermostability) was approximately 23%, the single mutant-like phenotype was approximately 42%, and wild type-like phenotype was approximately 34%. This distribution is very close to the values expected when the two thermostable mutations N218S and N181D can recombine with each other completely freely.

Figure 4:
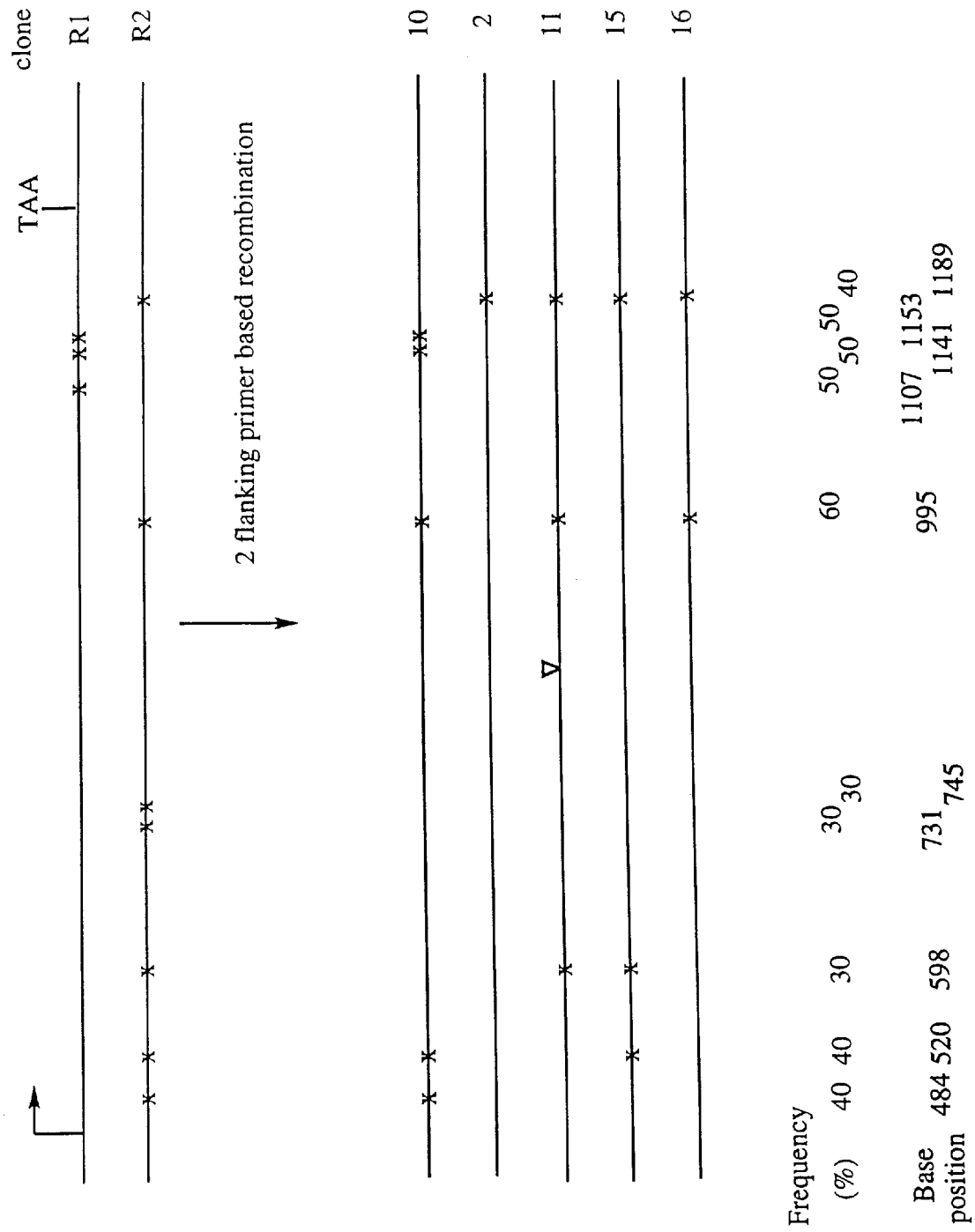
FIG. 4 is a diagrammatic representation of the results of the recombination of two genes using two flanking primers and staggered extension in accordance with the present invention. DNA sequences of five genes chosen from the recombined library are indicated, where x is a mutation present in the parental genes, and the triangle represents a new point mutation.

Twenty clones were randomly picked from *E. coli* HB101 gene library. Their plasmid DNAs were isolated and digested with NdeI and BamHI. Nine out of 20 (45%) had the inserts of correct size (approximately 1 kb). Thus, approximately 55% of the above library had no activity due to lack of the correct subtilisin E gene. These clones are not members of the subtilisin library and should be removed from our calculations. Taking into account this factor, we find that 55% of the library (25% active clones/45% clones with correct size insert) retained subtilisin activity. This activity profile indicates a point mutagenesis rate of less than 2 mutations per gene (36). Five clones with inserts of the correct size were sequenced. The results are summarized in FIG. 4. All five genes are recombination products with minimum crossovers varying from 1 to 4. Only one new point mutation was found in these five genes.

EXAMPLE 2

Use of Defined Flanking Primers and Staggered Extension to Recombine pNB Esterase Mutants The two-primer recombination method used here for pNB esterase is analogous to that described in Example 1 for subtilisin E. Two template pNB esterase mutant genes that differ at 14 bases are used. Both templates (61C7 and 4G4) are used in the plasmid form. Both target genes are present in the extension reaction at a concentration of 1 ng/ul. Flanking primers (RM1A and RM2A, Table 2) are added at a final concentration of 2 ng/ul (approximately 200-fold molar excess over template).

TABLE 2

Primers used in the recombination of the pNB esterase genes

| Primer | Sequence | | |
|---|---|---|---|
| RM1A | GAG CAC ATC AGA TCT ATT AAC | (SEQ. ID. NO: 3) | |
| RM2A | GGA GTG GCT CAC AGT CGG TGG | (SEQ. ID. NO: 4) | |

Clone 61C7 was isolated based on its activity in organic solvent and contains 13 DNA mutations vs. the wild-type sequence. Clone 4G4 was isolated for thermostability and contains 17 DNA mutations when compared with wild-type. Eight mutations are shared between them, due to common ancestry. The gene product from 4G4 is significantly more thermostable than the gene product from 61C7. Thus, one measure of recombination between the genes is the co-segregation of the high solvent activity and high thermostability or the loss of both properties in the recombined genes. In addition, recombination frequency and mutagenic rate can be ascertained by sequencing random clones.

For the pNB esterase gene, primer extension proceeds through 90 rounds of extension with a thermocycle consisting of 30 seconds at 94° C. followed by 15 seconds at 55° C. Aliquots (10 μl) are removed following cycle 20, 40, 60, 70, 80 and 90. Agarose gel electrophoresis reveals the formation of a low molecular weight 'smear' by cycle 20, which increases in average size and overall intensity at each successive sample point. By cycle 90, a pronounced smear is evident extending from 0.5 kb to 4 kb, and exhibiting maximal signal intensity at a size of approximately 2 kb (the length of the full length genes). The jump from half-length to full length genes appears to occur between cycles 60 and 70.

The intense smear is amplified through 6 cycles of polymerase chain reaction to more clearly define the full length recombined gene population. A minus-primer control is also amplified with flanking primers to determine the background due to residual template in the reaction mix. Band intensity from the primer extended gene population exceeds that of the control by greater than 10-fold, indicating that amplified, non-recombined template comprise only a small fraction of the amplified gene population.

The amplified recombined gene pool is digested with restriction enzymes XbaI and BamHI and ligated into the pNB106R expression vector described by Zock et al. (35). Transformation of ligated DNA into *E. coli* strain TG1 is done using the well characterized calcium chloride transformation procedure. Transformed colonies are selected on LB/agar plates containing 20 μg/ml tetracycline.

The mutagenic rate of the process is determined by measuring the percent of clones expressing an active esterase (20). In addition, colonies picked at random are sequenced and used to define the mutagenic frequency of the method and the efficiency of recombination.

EXAMPLE 3

Recombination of pNB Esterase Genes Using Interspersed Internal Defined Primers and Staggered Extension This example demonstrates that the interspersed defined primer recombination technique can produce novel sequences through point mutagenesis and recombination of mutations present in the parent sequences.

Experimental Design and Background Information

Figure 5:
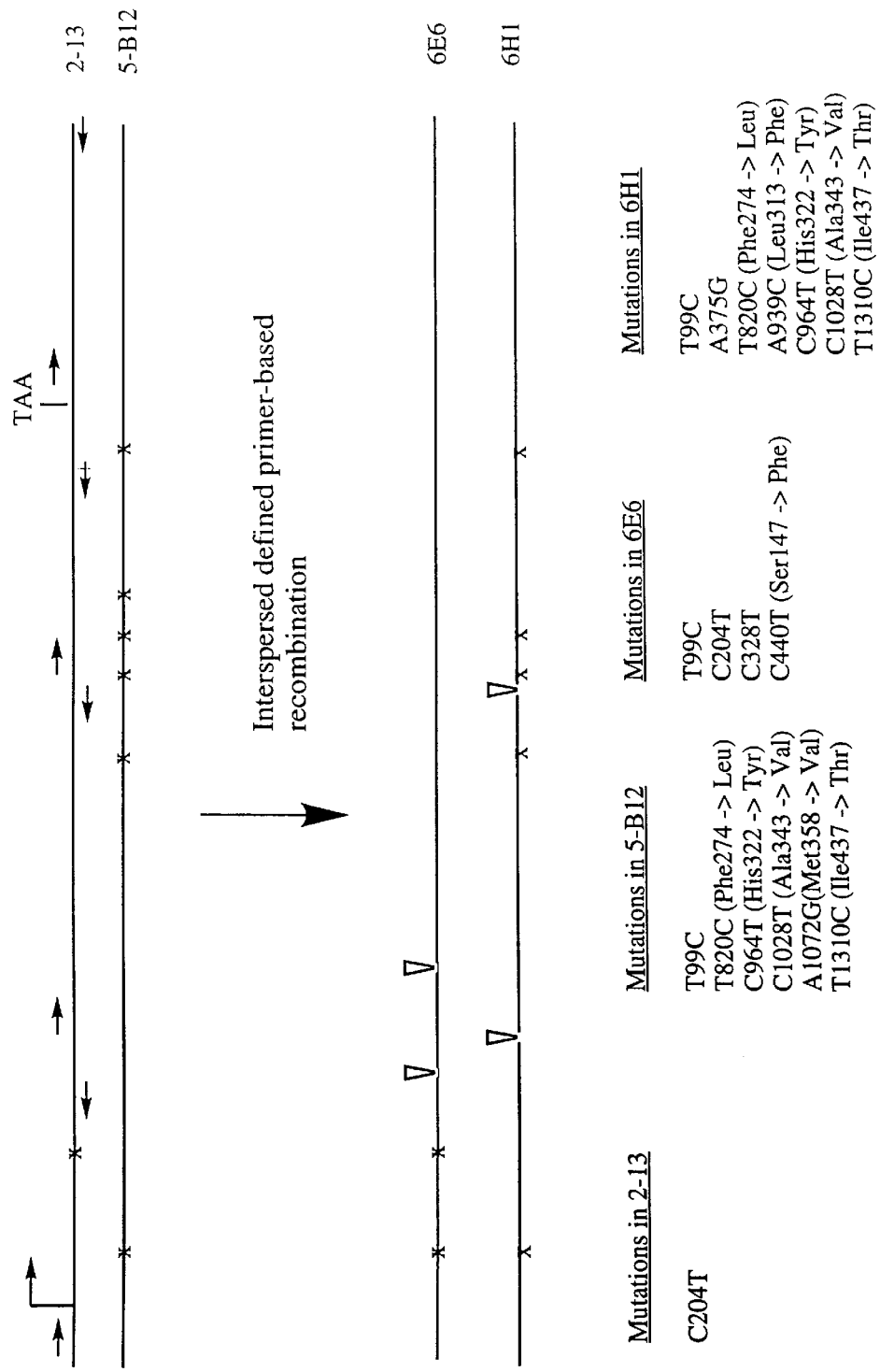
FIG. 5 is a diagrammatic representation of the sequences of the pNB esterase genes described in Example 3. Template genes 2–13 and 5-B12 were recombined using the defined primer approach. The positions of the primers are indicated by arrows, and the positions where the parental sequences differ from one another are indicated by x's. New point mutations are indicated by triangles. Mutations identified in these recombined genes are listed (only positions which differ in the parental sequences are listed). Both 6E6 and 6H1 are recombination products of the template genes.

Two pNB esterase genes (2-13 and 5-B12) were recombined using the defined primer recombination technique. Gene products from both 2-13 and 5-B12 are measurably more thermostable than wild-type. Gene 2-13 contains 9 mutations not originally present in, the wild-type sequence, while gene 5-B12 contains 14. The positions at which these two genes differ from one another are shown in FIG. 5.

Table 3 shows the sequences of the eight primers used in this example. Location (at the 5' end of the template gene) of oligo annealing to the template genes is indicated in the table, as is primer orientation (F indicates a forward primer, R indicates reverse). These primers are shown as arrows along gene 2-13 in FIG. 5.

TABLE 3

Sequences of primers used in this example

| name | orientation | location | sequence | | |
|---|---|---|---|---|---|
| RM1A | F | −76 | GAGCACATCAGATCTATTAAC | (SEQ. ID. NO: 3) | |
| RM2A | R | +454 | GGAGTGGCTCACAGTCGGTGG | (SEQ. ID. NO: 4) | |
| 52 | F | 400 | TTGAACTATCGGCTGGGGCGG | (SEQ. ID. NO: 5) | |
| 55 | F | 1000 | TTACTAGGGAAGCCGCTGGCA | (SEQ. ID. NO: 6) | |

TABLE 3-continued

Sequences of primers used in this example

| name | orientation | location | sequence | | | |
|------|-------------|----------|----------|---|---|---|
| S7   | F | 1400 | TCAGAGATTACGATCGAAAAC | (SEQ. | JD. NO: | 7) |
| 58   | R | 1280 | GGATTGTATCGTGTGAGAAAG | (SEQ. | ID. NO: | 8) |
| S10  | R | 880  | AATGCCGGAAGCAGCCCCTTC | (SEQ. | ID. NO: | 9) |
| S13  | R | 280  | CACGACAGGAAGATTTTGACT | (SEQ. | ID. NO: | 10) |

Materials and Methods
Defined-primer Based Recombination
1. Preparation of genes to be recombined. Plasmids containing the genes to be recombined were purified from transformed TG1 cells using the Qiaprep kit (Qiagen, Chatsworth, Calif.). Plasmids were quantitated by UV absorption and mixed 1:1 for a final concentration of 50 ng/ul.
2. Staggered extension PCR and reassembly. 4 μl of the plasmid mixture was used as template in a 100 μl standard reaction (1.5 mM MgCl$_2$, 50 mM KCl, 10 mM Tris-HCl pH 9.0, 0.1% Triton X-100, 0.2 mM dNTPs, 0.25 U Taq polymerase (Promega, Madison, Wis.)) which also contained 12.5 ng of each of the 8 primers. A control reaction which contained no primers was also assembled. Reactions were thermocycled through 100 cycles of 94° C., seconds; 55° C., 15 seconds. Checking an aliquot of the reaction on an agarose gel at this point showed the product to be a large smear (with no visible product in the no primer control).
3. DpnI digestion of the templates. 1 μl from the assembly reactions was then digested with DpnI to remove the template plasmid. The 10 μl DpnI digest contained 1×NEBuffer 4 and 5 U DpnI (both obtained from New England Biolabs, Beverly, Mass.) and was incubated at 37° C. for 45 minutes, followed by incubation at 70° C. for 10 minutes to heat kill the enzyme.
4. PCR amplification of the reassembled products. The 10 μl digest was then added to 90 μl of a standard PCR reaction (as described in step 2) containing 0.4 μM primers 5b (ACTTAATCTAGAGGGTATTA) (SEQ. ID. NO: 11) and 3b (AGCCTCGCGGGATCCCCGGG) (SEQ. ID. NO: 12) specific for the ends of the gene. After cycles of standard PCR (94° C., 30 seconds; 48° C., 30 seconds, 72° C., 1 minute) a strong band of the correct size (2 kb) was visible when the reaction was checked on an agarose gel, while only a very faint band was visible in the lane from the no-primer control. The product band was purified and cloned back into the expression plasmid pNB106R and transformed by electroporation into TG1 cells.

Results

Four 96 well plates of colonies resulting from this transformation were assayed for pNB esterase initial activity and thermostability. Approximately 60% of the clones exhibited initial activity and thermostabilty within 20% of the parental gene values. Very few (10%) of the clones were inactive (less than 10% of parent initial activity values). These results suggest a low rate of mutagenesis. Four mutants with the highest thermostability values were sequenced. Two clones (6E6 and 6H1) were the result of recombination between the parental genes (FIG. 5). One of the remaining two clones contained a novel point mutation, and one showed no difference from parent 5B12. The combination of mutations T99C and C204T in mutant 6E6 is evidence for a recombination event between these two sites. In addition, mutant 6H1 shows the loss of mutation A1072G (but the retention of mutations C1038T and T1310C), which is evidence for two recombination events (one between sites 1028 and 1072, and another between 1072 and 1310). A total of five new point mutations were found in the four genes sequenced.

EXAMPLE 4

Recombination of Two Thermostable Subtilisin E Variants Using Internal Defined Primers and Staggered Extension This example demonstrates that the defined primer recombination technique can produce novel sequences containing new combinations of mutations present in the parent sequences. It further demonstrates the utility of the defined primer recombination technique to obtain further improvements in enzyme performance (here, thermostability). This example further shows that the defined primers can bias the recombination so that recombination appears most often in the portion of the sequence defined by the primers (inside the primers). Furthermore, this example shows that specific mutations can be introduced into the recombined sequences by using the appropriate defined primer sequence(s) containing the desired mutation(s).

Figure 6:
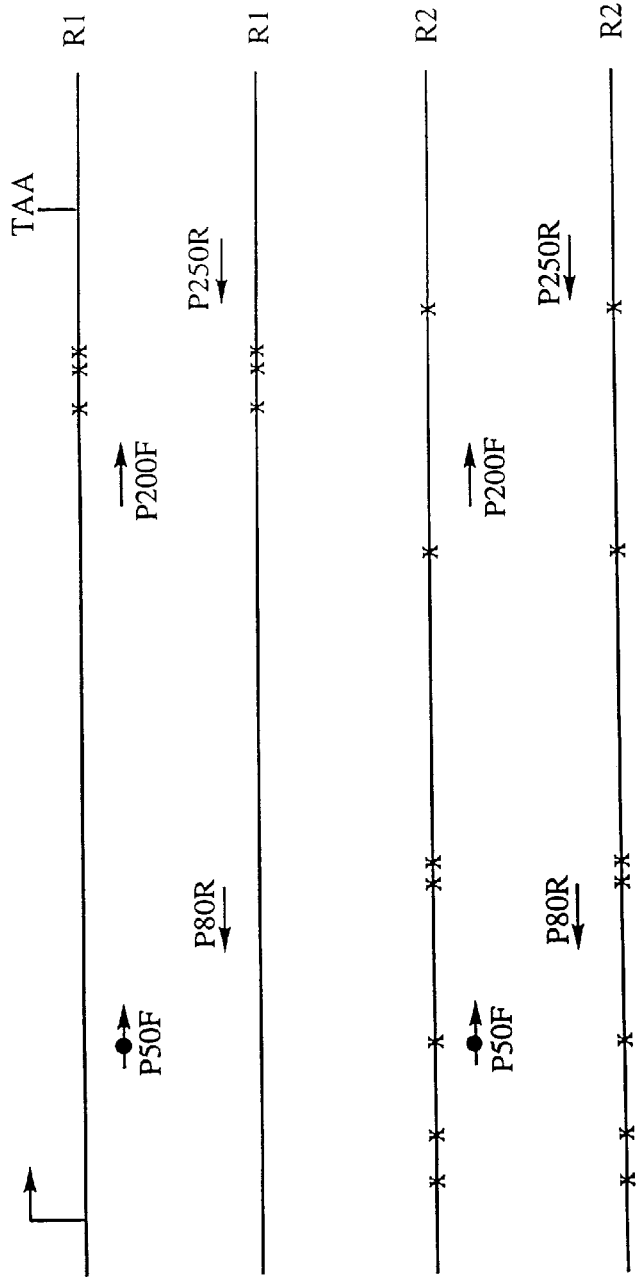
FIG. 6 shows the positions and sequences of the four defined internal primers used to generate recombined genes from template genes R1 and R2 by interspersed primer-based recombination. Primer P50F contains a mutation (A→T at base position 598) which simultaneously eliminates a HindIII restriction site and adds a new unique NheI site. Gene R2 also contains a mutation A→G at the same base position, which eliminates the HindIII site.

Genes encoding two thermostable subtilisin E variants of Example 1 (R1 and R2) were recombined using the defined primer recombination procedure with internal primers. FIG. 6 shows the four defined internal primers used to generate recombined progeny genes from template genes R1 and R2 in this example. Primer P50F contains a mutation (A→T at base position 598) which eliminates a HindIII restriction site and simultaneously adds a new unique NheI site. This primer is used to demonstrate that specific mutations can also be introduced into the population of recombined sequences by specific design of the defined primer. Gene R2 also contains a mutation A→G at the same base position, which eliminates the HindIII site. Thus restriction analysis (cutting by NheI and HindIII) of random clones sampled from the recombined library will indicate the efficiency of recombination and of the introduction of a specific mutation via the mutagenic primer. Sequence analysis of randomly-picked (unscreened) clones provides further information on the recombination and mutagenesis events occurring during defined primer-based recombination.

Materials and Methods
Defined-primer Based Recombination

A version of the defined primer based recombination illustrated in FIG. 2 was carried out with the addition of StEP.
1. Preparation of genes to be recombined. About 10 ug of plasmids containing R1 and R2 gene were digested at 37° C. for 1 hour with NdeI and BamHI (30 U each) in 50 μl of 1× buffer B (Boehringer Mannheim, Indianapolis, Ind.). Inserts of approximately 1 kb were purified from 0.8% preparative agarose gels using QIAEX II gel extraction kit. The DNA inserts were dissolved in 10 mM Tris-HCl (pH 7.4). The DNA concentrations were estimated, and the inserts were mixed 1:1 for a concentration of 50 ng/ul.

2. Staggered extension PCR and reassembly. Conditions (100 ul final volume): about 100 ng inserts were used as template, 50 ng of each of 4 internal primers, 1× Taq buffer, 0.2 mM of each dNTP, 1.5 mM MgCl$_2$ and 0.25 U Taq polymerase. Program: 7 cycles of 30 seconds at 94° C., 15 seconds at 55° C., followed by another 10 cycles of 30 seconds at 94° C., 15 seconds at 55° C., 5 seconds at 72° C. (staggered extension), followed by 53 cycles of 30 seconds at 94° C., 15 seconds at 55° C., 1 minute at 72° C. (gene assembly).

3. DpnI digestion of the templates. 1 μl of this reaction was diluted up to 9.5 μl with dH$_2$O and 0.5 μl of DpnI restriction enzyme was added to digest the DNA template for 45 minutes, followed by incubation at 70° C. for 10 minutes and then this 10 ul was used as template in a 10-cycle PCR reaction.

4. PCR amplification of reassembled products. PCR conditions (100 μl final volume): 30 pmol of each outside primer P5N and P3B, 1× Taq buffer, 0.2 mM of each dNTP and 2.5 U of Taq polymerase. PCR program: 10 cycles of 30 seconds at 94° C., 30 seconds at 55° C., 1 minute at 72° C. This program gave a single band at the correct size. The product was purified and subcloned into pBE3 shuttle vector. This gene library was amplified in *E. coli* HB101 and transferred into *B. subtilis* DB428 competent cells for expression and screening, as described elsewhere (35). Thermostability of enzyme variants was determined in the 96-well plate format described previously (33).

DNA Sequencing

Ten *E. coli* HB101 transformants were chosen for sequencing. Genes were purified using QIAprep spin plasmid miniprep kit to obtain sequencing quality DNA. Sequencing was done on an ABI 373 DNA Sequencing System using the Dye Terminator Cycle Sequencing kit (Perkin-Elmer, Branchburg, N.J.).

Results

1) Restriction Analysis

Figure 7:
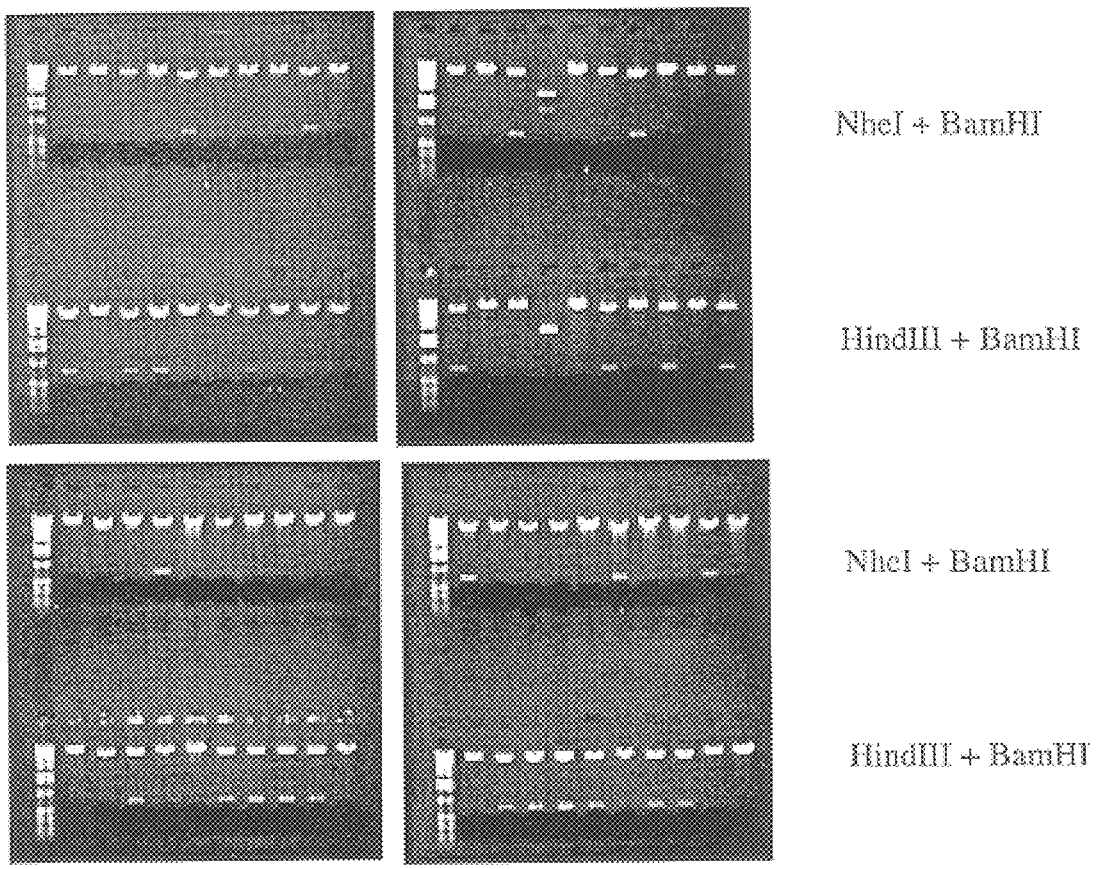
FIG. 7 is an electrophoresis gel which shows the results of the restriction-digestion analysis of plasmids from the 40 clones.

Forty clones randomly picked from the recombined library were digested with restriction enzymes NheI and BamHI. In a separate experiment the same forty plasmids were digested with HindIII and BamHI. These reaction products were analyzed by gel electrophoresis. As shown in FIG. 7, eight out of 40 clones (approximately 20%) contain the newly introduced NheI restriction site, demonstrating that the mutagenic primer has indeed been able to introduce the specified mutation into the population.

2) DNA Sequence Analysis

Figure 8:
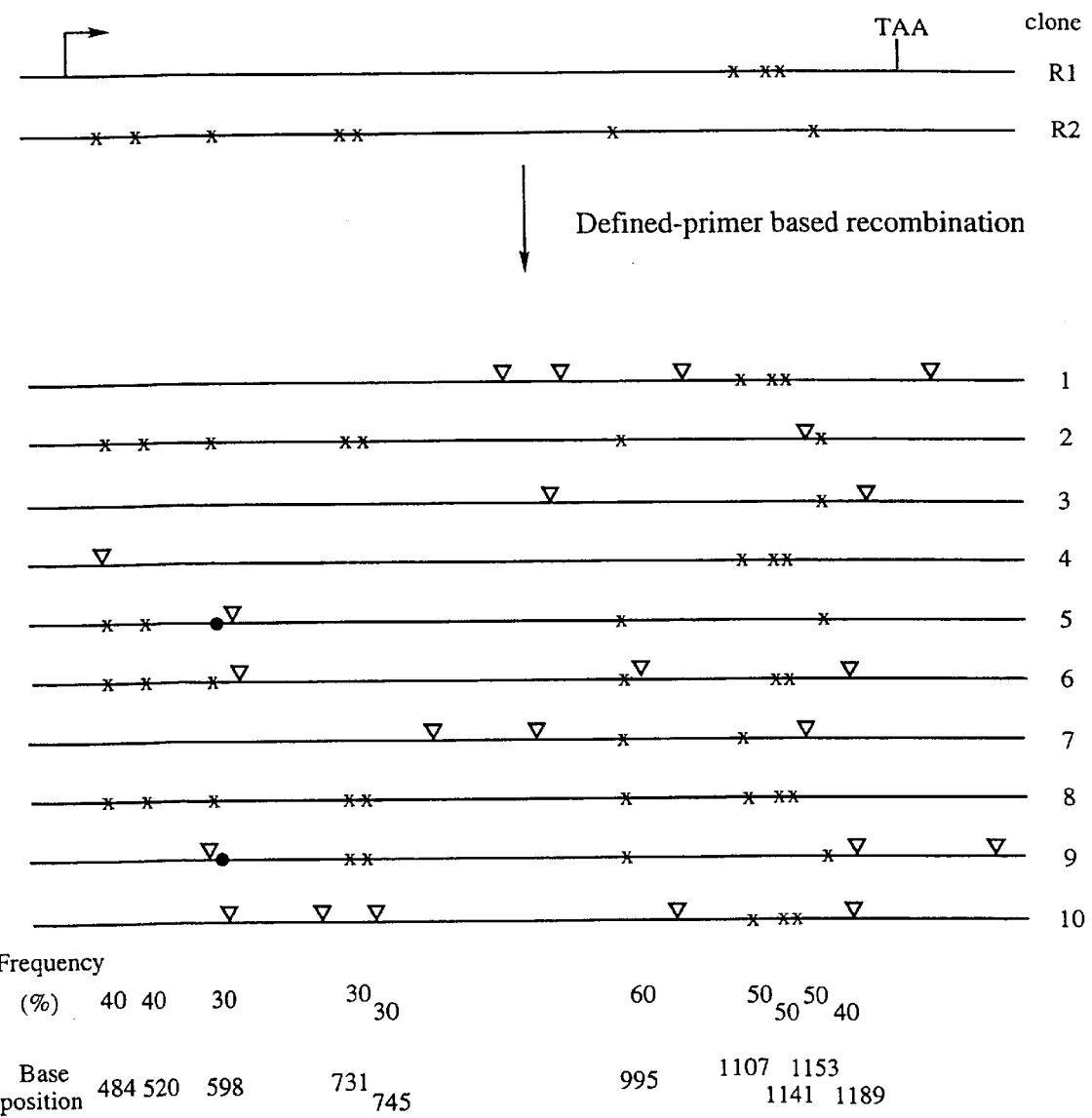
FIG. 8 shows the results of sequencing ten genes from the defined primer-based recombination library. Lines represent 986-bp of subtilisin E gene including 45 nt of its prosequence, the entire mature sequence and 113 nt after the stop codon. Crosses indicate positions of mutations from parent gene R1 and R2, while triangles indicate positions of new point mutations introduced during the recombination procedure. Circles represent the mutation introduced by the mutagenic primer P50F.

The first ten randomly picked clones were subjected to sequence analysis, and the results are summarized in FIG. 8. A minimum of 6 out of the 10 genes have undergone recombination. Among these 6 genes, the minimal crossover events (recombination) between genes R1 and R2 vary from 1 to 4. All visible crossovers occurred within the region defined by the four primers. Mutations outside this region are rarely, if ever, recombined, as shown by the fact that there is no recombination between the two mutations at base positions 484 and 520. These results show that the defined primers can bias recombination so that it appears most often in the portion of the sequence defined by the primers (inside the primers). Mutations very close together also tend to remain together (for example, base substitutions 731 and 745 and base substitutions 1141 and 1153 always remain as a pair). However, the sequence of clone 7 shows that two mutations as close as 33 bases apart can be recombined (base position at 1107 and 1141).

Twenty-three new point mutations were introduced in the ten genes during the process. This error rate of 0.23% corresponds to 2–3 new point mutations per gene, which is a rate that has been determined optimal for generating mutant libraries for directed enzyme evolution (15). The mutation types are listed in Table 4. Mutations are mainly transitions and are evenly distributed along the gene.

TABLE 4

New point mutations identified in ten recombined genes

| Transition | Frequency | Transversion | Frequency |
|---|---|---|---|
| G→A | 4 | A→T | 1 |
| A→G | 4 | A→C | 1 |
| C→T | 3 | C→A | 1 |
| T→C | 5 | C→G | 0 |
|  |  | G→C | 1 |
|  |  | G→T | 0 |
|  |  | T→A | 3 |
|  |  | T→G | 0 |

A total of 9860 bases were sequenced. The mutation rate was 0.23%

4) Phenotypic Analysis

Approximately 450 *B. subtilis* DB428 clones were picked and grown in SG medium supplemented with 20 ug/ml kanamycin in 96-well plates. Approximately 56% of the clones expressed active enzymes. From previous experience, we know that this level of inactivation indicates a mutation rate on the order of 2–3 mutations per gene (35). Approximately 5% clones showed double mutant (N181D+N218S)-like phenotypes (which is below the expected 25% value for random recombination alone due primarily to point mutagenesis). (DNA sequencing showed that two clones, 7 and 8, from the ten randomly picked clones contain both N218S and N181D mutations.)

EXAMPLE 6

Optimization of the *Actinoplanes utahensis* ECB Deacylase by the Random-Priming Recombination Method In this example, the method is used to generate short DNA fragments from denatured, linear, double-stranded DNA (e.g., restriction fragments purified by gel electrophoresis; 22). The purified DNA, mixed with a molar excess of primers, is denatured by boiling, and synthesis is then carried out using the Klenow fragment of *E. coli* DNA polymerase I. This enzyme lacks 5'→3' exonuclease activity, so that the random priming product is synthesized exclusively by primer extension and is not degraded by exonuclease. The reaction is carried out at pH 6.6, where the 3'→5' exonuclease activity of the enzyme is much reduced (36). These conditions favor random initiation of synthesis.

The procedure involves the following steps:

1. Cleave the DNA of interest with appropriate restriction endonuclease(s) and purify the DNA fragment of interest by gel electrophoresis using Wizard PCR Prep Kit (Promega, Madison, Wis.). As an example, the *Actinoplanes utahensis* ECB deacylase gene was cleaved as a 2.4 kb-long Xho I-Psh AI fragment from the recombinant plasmid pSHP100. It was essential to linearize the DNA for the subsequent denaturation step. The fragment was purified by agarose gel electrophoresis using the Wizard PCR Prep Kit (Promega, Madison, Wis.) (FIG. 9, step (a)). Gel purification was also essential in order to remove the restriction endonuclease buffer from the DNA, since the Mg$^{2+}$ ions make it difficult to denature the DNA in the next step.

2. 400 ng (about 0.51 pmol) of the double-stranded DNA dissolved in H$_2$O was mixed with 2.75 μg (about 1.39 nmol) of dp(N)$_6$ random primers. After immersion in boiling water for 3 minutes, the mixture was placed immediately in an ice/ethanol bath.

Figure 9:
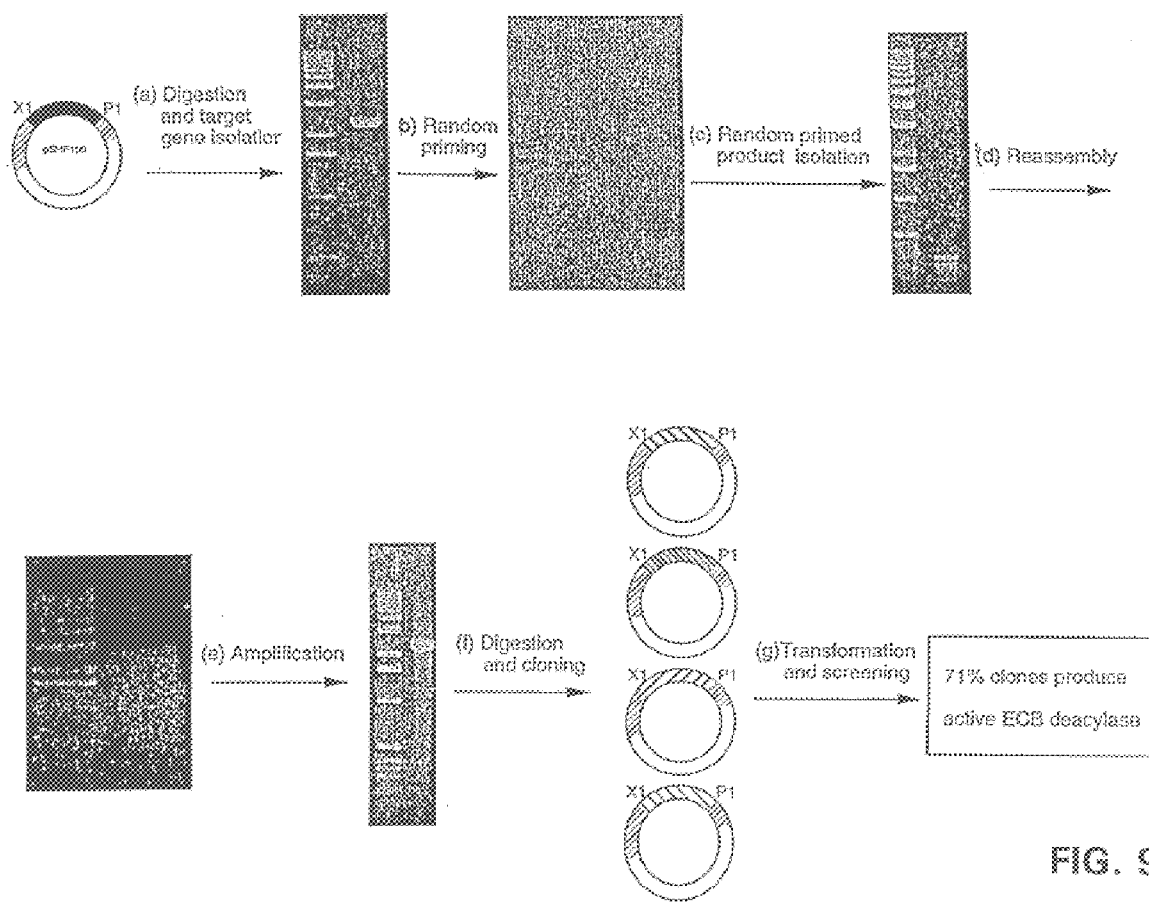
FIG. 9 depicts the results of applying the random-sequence primer recombination method to the gene for *Actinoplanes utahensis* ECB deacylase. (a) The 2.4 kb ECB deacylase gene was purified from an agarose gel. (b) The size of the random priming products ranged from 100 to 500 bases. (c) Fragments shorter than 300 bases were isolated. (d) The purified fragments were used to reassemble the full-length gene with a smear background. (e) A single PCR product of the same size as the ECB deacylase gene was obtained after conventional PCR with the two primers located at the start and stop regions of this gene. (f) After digestion with Xho I and Psh AI, the PCR product was cloned into a modified pIJ702 vector to form a mutant library. (g) Introducing this library into *Streptomyces lividans* TK23 resulted in approximately 71% clones producing the active ECB deacylase.

The size of the random priming products is an inverse function of the concentration of primer (33). The presence of high concentrations of primer is thought to lead to steric hindrance. Under the reaction conditions described here the random priming products are approximately 200–400 bp, as determined by electrophoresis through an alkaline agarose gel (FIG. 9 step b).

3. Ten μl of 10× reaction buffer [10× buffer: 900 mM HEPES, pH 6.6; 0.1 M magnesium chloride, 10 mM dithiothreitol, and 5 mM each dATP, dCTP, dGTP and dTTP) was added to the denatured sample, and the total volume of the reaction mixture was brought up to 95 μl with H$_2$O.

4. Ten units (about 5 μl) of the Klenow fragment of *E.coli* DNA polymerase I was added. All the components were mixed by gently tapping the outside of the tube and were centrifuged at 12,000 g for 1–2 seconds in a microfuge to move all the liquid to the bottom. The reaction was carried out at 22° C. for 35 minutes.

The rate of the extension depends upon the concentrations of the template and the four nucleotide precursors. Because the reaction was carried out under conditions that minimize exonucleolytic digestion, the newly synthesized products were not degraded to a detectable extent.

5. After 35 minutes at 22° C., the reaction was terminated by cooling the sample to 0° C. on ice. 100 μl of ice-cold H$_2$O was added to the reaction mixture.

6. The random primed products were purified by passing the whole reaction mixture through Centricon-100 (to remove the template and proteins) and Centricon-10 filters (to remove the primers and fragments less than 50 bases), successively. Centricon filters are available from Amicon Inc (Berverly, Mass.). The retentate fraction (about 85 μl in volume) was recovered from Centricon-10. This fraction contained the desired random priming products (FIG. 9, step c) and was used for whole gene reassembly.

Reassembly of the whole gene was accomplished by the following steps:

1. For reassembly by PCR, 5 μl of the random-primed DNA fragments from Centricon-10, 20 μl of 2×PCR pre-mix (5-fold diluted cloned Pfu buffer, 0.5 mM each DNTP, 0.1 U/μl cloned Pfu polymerase (Stratagene, La Jolla, Calif.)), 8 μl of 30% (v/v) glycerol and 7 μl of H$_2$O were mixed on ice. Since the concentration of the random-primed DNA fragments used for reassembly is the most important variable, it is useful to set up several separate reactions with different concentrations to establish the preferred concentration.

2. After incubation at 96° C. for 6 minutes, 40 thermocycles were performed, each with 1.5 minutes at 95° C., 1.0 minutes at 55° C. and 1.5 minutes+5 second/cycle at 72° C., with the extension step of the last cycle proceeding at 72° C. for 10 minutes, in a DNA Engine PTC-200 (MJ Research Inc., Watertown, Mass.) apparatus without adding any mineral oil.

3. 3 μl aliquots at cycles 20, 30 and 40 were removed from the reaction mixture and analyzed by agarose gel electrophoresis. The reassembled PCR product at 40 cycles contained the correct size product in a smear of larger and smaller sizes (see FIG. 9, step d).

The correctly reassembled product of this first PCR was further amplified in a second PCR reaction which contained the PCR primers complementary to the ends of the template DNA. The amplification procedure was as follows:

1. 2.0 μl of the PCR reassembly aliquots were used as template in 100-μl standard PCR reactions, which contained 0.2 mM each primers of xhoF28 (5' GGTAGAGCGAGTCTCGAGGGGGAGATGC3') (SEQ. ID. NO: 13) and pshR22 (5' AGCCGGCGTGACGTGGGT-CAGC 3') (SEQ. ID. NO: 14), 1.5 mM MgCl$_2$, 10 mM Tris-HCl [pH 9.0], 50 mM KCl, 200 μM each of the four dNTPs, 6% (v/v) glycerol, 2.5 U of Taq polymerase (Promega, Madison, Wis.) and 2.5 U of Pfu polymerase (Stratagene, La Jolla, Calif.).

2. After incubation at 96° C. for 5 minutes, thermocycles were performed, each with 1.5 minutes at 95° C., 1.0 minutes at 55° C. and 1.5 minutes at 72° C., followed by additional 15 thermocycles of 1.5 minutes at 95° C., 1.0 minutes at 55° C. and 1.5 minutes+5 second/cycle at 72° C. with the extension step of the last cycle proceeding at 72° C. for 10 minutes, in a DNA Engine PTC-200 (MJ Research Inc., Watertown, Mass.) apparatus without adding any mineral oil.

3. The amplification resulted in a large amount of PCR product with the correct size of the ECB deacylase whole gene (FIG. 9, step e).

Cloning was accomplished as follows:

1. The PCR product of ECB deacylase gene was digested with Xho I and Psh AI restriction enzymes, and cloned into a modified pIJ702 vector. 2. *S. lividans* TK23 protoplasts were transformed with the above ligation mixture to form a mutant library.

In situ Screening the ECB Deacylase Mutants

Each transformant within the *S. lividans* TK23 library obtained as described above was screened for deacylase activity with an in situ plate assay method using ECB as substrate. Transformed protoplasts were allowed to regenerate on R2YE agar plates by incubation at 30° C. for 24 hours and to develop in the presence of thiostrepton for further 48–72 hours. When the colonies grew to proper size, 6 ml of 45° C. purified-agarose (Sigma) solution containing 0.5 mg/ml ECB in 0.1 M sodium acetate buffer (pH 5.5) was poured on top of each R2YE-agar plate and allowed to further develop for 18–24 hours at 37° C. Colonies surrounded by a clearing zone larger than that of a control colony containing wild-type recombinant plasmid pSHP150-2 were indicative of more efficient ECB hydrolysis resulting from improved enzyme properties or improved enzyme expression and secretion level, and were chosen as potential positive mutants. These colonies were picked for subsequent preservation and manipulation.

HPLC Assay of the ECB Deacylase Mutants

Single positive transformants were inoculated into 20 ml fermentation medium containing 5 μg/ml thiostrepton and allowed to grow at 30° C. for 48 hours. At this step, all cultures were subjected to HPLC assay using ECB as substrate. 100 μl of whole broth was used for an HPLC reaction at 30° C. for 30 minutes in the presence of 0.1 M NaAc (pH 5.5), 10% (v/v) MeOH and 200 μg/ml of ECB substrate. 20 μl of each reaction mixture was loaded onto a PolyLC polyhydroxyethyl aspartamide column (4.6×100 mm) and eluted by acetonitrile gradient at a flow rate of 2.2 ml/min. The ECB-nucleus was detected at 225 nm.

Purification of the ECB Deacylase Mutants

After the HPLC assay, 2.0 ml pre-cultures of all potential positive mutants were then used to inoculate 50-ml fermentation medium and allowed to grow at 30° C., 280 rpm for 96 hours. These 50-ml cultures were then centrifuged at 7,000 g for 10 minutes. The supernatants were re-centrifuged at 16,000 g for 20 minutes. The supernatants containing the ECB deacylase mutant enzymes were stored at −20° C.

The supernatants from the positive mutants were further concentrated to 1/30 their original volume with an Amicon filtration unit with molecular weight cutoff of 10 kD. The resulting enzyme samples were diluted with an equal volume of 50 mM $KH_2PO_4$ (pH 6.0) buffer and 1.0 ml was applied to Hi-Trap ion exchange column. The binding buffer was 50 mM $KH_2PO_4$ (pH 6.0), and the elution buffer was 50 mM $KH_2PO_4$ (pH 6.0) and 1.0 M NaCl. A linear gradient from 0 to 1.0 M NaCl was applied in 8 column volumes with a flow rate of 2.7 ml/min. The ECB deacylase mutant fraction eluted at 0.3 M NaCl and was concentrated and buffer exchanged into 50 mM $KH_2PO_4$ (pH 6.0) in Amicon Centricon-10units. Enzyme purity was verified by SDS-PAGE, and the concentration was determined using the Bio-Rad Protein Assay.

Specific Activity Assay of the ECB Deacylase Mutants 4.0 μg of each purified ECB deacylase mutant was used for the activity assay at 30° C. for 0–60 minutes in the presence of 0.1 M NaAc (pH 5.5), 10% (v/v) MeOH and 200 μg/ml of ECB substrate. 20 μl of each reaction mixture was loaded onto a PolyLC polyhydroxyethyl aspartamide column (4.6×100 mm) and eluted with an acetonitrile gradient at a flow rate of 2.2 ml/min. The reaction products were monitored at 225 nm and recorded on an IBM PC data acquisition system. The ECB nucleus peak was numerically integrated and used to calculate the specific activity of each mutant.

Figure 10:
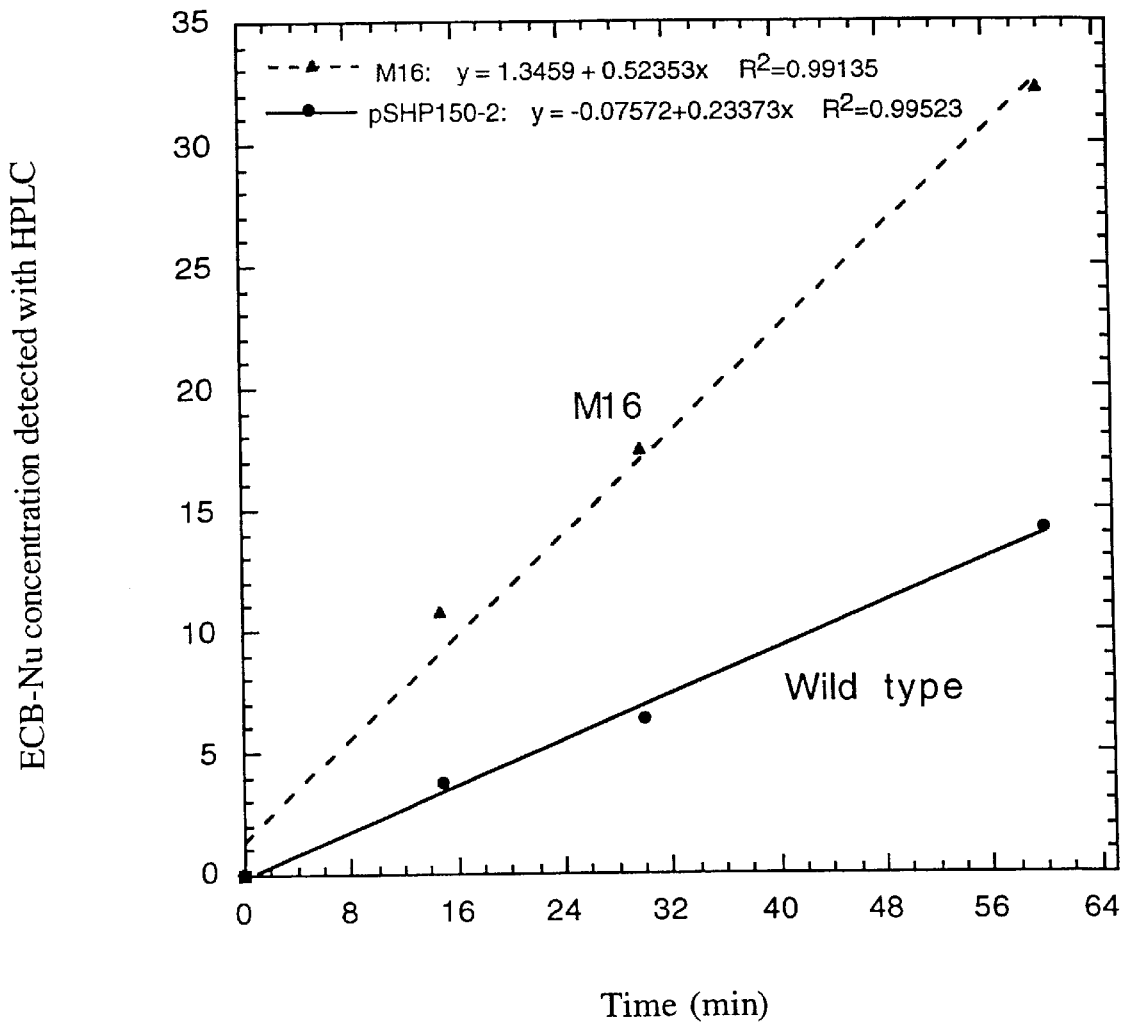
FIG. 10 shows the specific activity of the wild-type ECB deacylase and mutant M16 obtained in accordance with the present invention.
Figure 11:
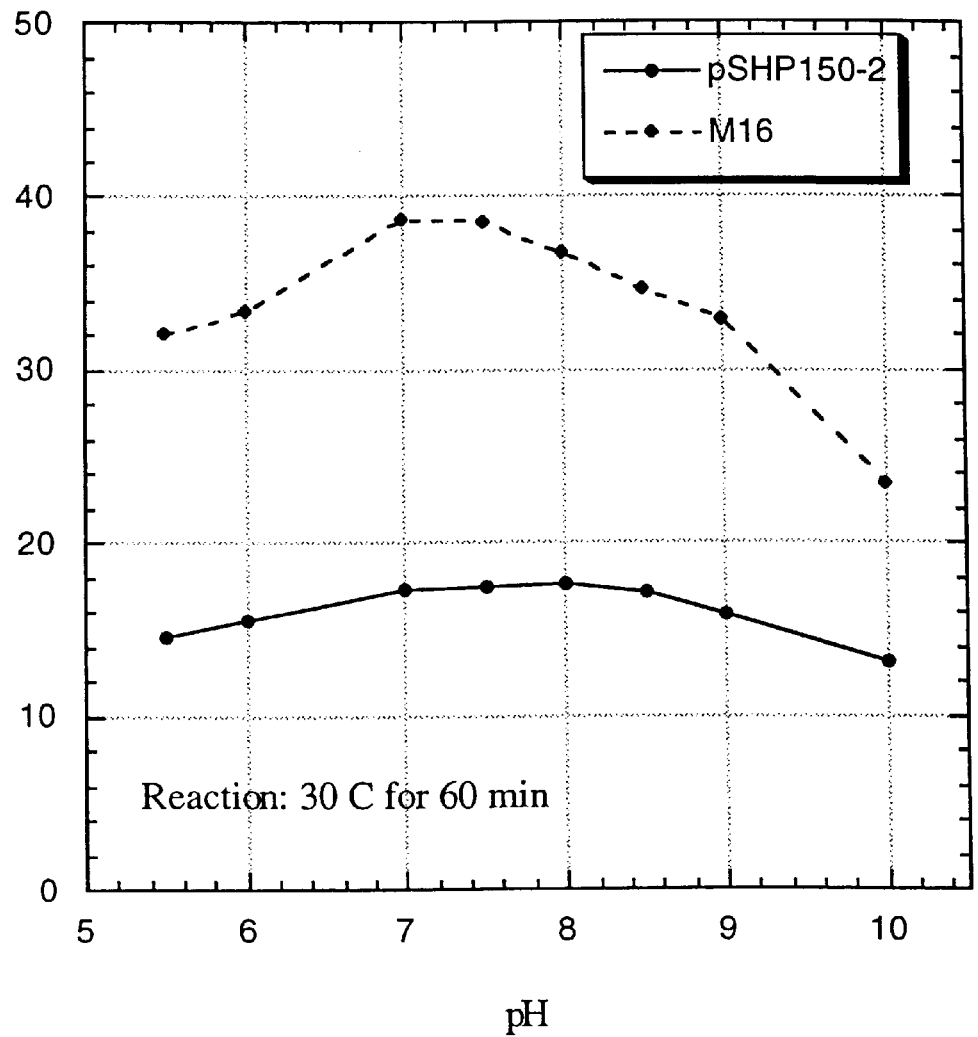
FIG. 11 shows pH profiles of activity of the wild-type ECB deacylase and mutant M16 obtained in accordance with the present invention.

As shown in FIG. 10, after only one round of applying this random-priming based technique on the wild-type ECB deacylase gene, one mutant (M16) from 2,012 original transformants was found to possess 2.4 times the specific activity of the wild-type enzyme. FIG. 11 shows that the activity of M16 has been increased relative to that of the wild-type enzyme over a broad pH range.

EXAMPLE 7

Improving the Thermostability Bacillus subtilis Subtilisin E Using the Random-sequence Primer Recombination Method This example demonstrates the use of various DNA polymerases for primer-based recombination. It further demonstrates the stabilization of subtilisin E by recombination.

Genes R1 and R2 encoding the two thermostable subtilisin E variants described in Example 1 were chosen as the templates for recombination.

(1) Target Gene Preparation

Subtilisin E thermostable mutant genes R1 and R2 (FIG. 11) were subjected to random primed DNA synthesis. The 986-bp fragment including 45 nt of subtilisin E prosequence, the entire mature sequence and 113 nt after the stop codon were obtained by double digestion of plasmid pBE3 with BamHI and NdeI and purified from a 0.8% agarose gel using the Wizard PCR Prep Kit (Promega, Madison, Wis.). It was essential to linearize the DNA for the subsequent denaturation step. Gel purification was also essential in order to remove the restriction endonuclease buffer from the DNA, since the $Mg^{2+}$ ions make it difficult to denature the DNA in the next step.

(2) Random Primed DNA Synthesis

Random primed DNA synthesis used to generate short DNA fragments from denatured, linear, double-stranded DNA. The purified B. subtilis subtilisin E mutant genes, mixed with a molar excess of primers, were denatured by boiling, and synthesis was then carried out using one of the following DNA polymerases: the Klenow fragment of E. coli DNA polymerase I, bacteriophage T4 DNA polymerase and T7 sequenase version 2.0 DNA polymerase.

Under its optimal performance conditions (29), bacteriophage T4 DNA polymerase gives similar synthesis results as the Klenow fragment does. When T7 sequenase version 2.0 DNA polymerase (31, 32) is used, the lengths of the synthesized DNA fragments are usually larger. Some amount of $MnCl_2$ has to be included during the synthesis in order to control the lengths of the synthesized fragments within 50–400 bases.

Short, nascent DNA fragments can also be generated with PCR using the Stoffel fragment of Taq DNA polymerase or Pfu DNA polymerase. An important consideration is to identify by routine experimentation the reaction conditions which ensure that the short random primers can anneal to the templates and give sufficient DNA amplification at higher temperatures. We have found that random primers as short as $dp(N)_{12}$ can be used with PCR to generate fragments.

2.1 Random Primed DNA Synthesis with the Klenow Fragment

The Klenow fragment of E. coli DNA polymerase I lacks 5'→3' exonuclease activity, so that the random priming product is synthesized exclusively by primer extension and is not degraded by exonuclease. The reaction was carried out at pH 6.6, where the 3'→5' exonuclease activity of the enzyme is much reduced (36). These conditions favor random initiation of synthesis.

1. 200 ng (about 0.7 pmol) of R1 DNA and equal amount of R2 DNA dissolved in $H_2O$ was mixed with 13.25 μg (about 6.7 nmol) of $dp(N)_6$ random primers. After immersion in boiling water for 5 minutes, the mixture was placed immediately in an ice/ethanol bath.

The size of the random priming products is an inverse function of the concentration of primer (30). The presence of high concentrations of primer is thought to lead to steric hindrance. Under the reaction conditions described here the random priming products are approximately 50–500 bp, as determined by agarose gel electrophoresis.

2. Ten μl of 10× reaction buffer [10× buffer: 900 mM HEPES, pH 6.6; 0.1 M magnesium chloride, 20 mM dithiothreitol, and 5 mM each dATP, dCTP, dGTP and dTTP] was added to the denatured sample, and the total volume of the reaction mixture was brought up to 95 μl with $H_2O$.

3. Ten units (about 5 μl) of the Klenow fragment of E. coli DNA polymerase I (Boehringer Mannheim, Indianapolis, Ind.) was added. All the components were mixed by gently tapping the outside of the tube and were centrifuged at 12,000 g for 1–2 seconds in a microfuge to move all the liquid to the bottom. The reaction was carried out at 22° C. for 3 hours.

The rate of the extension depends upon the concentrations of the template and the four nucleotide precursors. Because the reaction was carried out under conditions that minimize exonucleolytic digestion, the newly synthesized products were not degraded to a detectable extent.

4. After 3 hours at 22° C., the reaction was terminated by cooling the sample to 0° C. on ice. 100 μl of ice-cold $H_2O$ was added to the reaction mixture.

5. The random primed products were purified by passing the whole reaction mixture through Microcon-100 (Amicon, Beverly Mass.) (to remove the template and proteins) and Microcon-10 filters (to remove the primers and fragments less than 40 bases), successively. The retentate fraction (about 65 μl in volume) was recovered from the Microcon-10. This fraction containing the desired random priming products was buffer-exchanged against PCR reaction buffer with the new Microcon-10 further use in whole gene reassembly.

2.2 Random Primed DNA Synthesis with Bacteriophage T4 DNA Polymerase

Bacteriophage T4 DNA polymerase and the Klenow fragment of E.coli DNA polymerase I are similar in that each possesses a 5'–3' polymerase activity and a 3'–5' exonuclease activity. The exonucleases activity of bacteriophage T4 DNA polymerase is more than 200 times that of the Klenow fragment. Since it does not displace the short oligonucleotide primers from single-stranded DNA templates (23), the efficiency of mutagenesis is different from the Klenow fragment.

1. 200 ng (about 0.7 pmol) of R1 DNA and equal amount of R2 DNA dissolved in $H_2O$ was mixed with 13.25 μg (about 6.7 nmol) of $dp(N)_6$ random primers. After immersion in boiling water for 5 minutes, the mixture was placed immediately in an ice/ethanol bath. The presence of high concentrations of primer is thought to lead to steric hindrance.
2. Ten μl of 10 × reaction buffer [10× buffer: 500 mM Tris-HCl, pH 8.8; 150 mM $(NH_4)_2SO_4$; 70 mM magnesium chloride, 100 mM 2-mercaptoethanol, 0.2 mg/ml bovine serum albumin and 2 mM each dATP, dCTP, dGTP and dTTP) was added to the denatured sample, and the total volume of the reaction mixture was brought up to 90 μl with $H_2O$.
3. Ten units (about 10 μl) of the T4 DNA polymerase I (Boehringer Mannheim, Indianapolis, Ind.) was added. All the components were mixed by gently tapping the outside of the tube and were centrifuged at 12,000 g for 1–2 seconds in a microfuge to move all the liquid to the bottom. The reaction was carried out at 37° C. for 30 minutes. Under the reaction conditions described here the random priming products are approximately 50–500 bp.
4. After 30 minutes at 37° C., the reaction was terminated by cooling the sample to 0° C. on ice. 100 μl of ice-cold $H_2O$ was added to the reaction mixture.
5. The random primed products were purified by passing the whole reaction mixture through Microcon-100 (to remove the template and proteins) and Microcon-10 filters (to remove the primers and fragments less than 40 bases), successively. The retentate fraction (about 65 μl in volume) was recovered from the Microcon-10. This fraction containing the desired random priming products was buffer-exchanged against PCR reaction buffer with the new Microcon-10 further use in whole gene reassembly.

2.3 Random Primed DNA Synthesis with the T7 Sequenase v2.0 DNA Polymerase

Since the T7 sequenase v2.0 DNA polymerase lacks exonuclease activity and is highly processive, the average length of DNA synthesized is greater than that of DNAs synthesized by the Klenow fragment or T4 DNA polymerase. But in the presence of proper amount of $MnCl_2$ in the reaction, the size of the synthesized fragments can be controlled to less than 400 bps.

1. 200 ng (about 0.7 pmol) of R1 DNA and equal amount of R2 DNA dissolved in $H_2O$ was mixed with 13.25 μg (about 6.7 nmol) of $dp(N)_6$ random primers. After immersion in boiling water for 5 minutes, the mixture was placed immediately in an ice/ethanol bath. The presence of high concentrations of primer is thought to lead to steric hindrance.
2. Ten μl of 10× reaction buffer [10× buffer: 400 mM Tris-HCl, pH 7.5; 200 mM magnesium chloride, 500 mM NaCl, 3 mM $MnCl_2$, and 3 mM each dATP, dCTP, dGTP and dTTP) was added to the denatured sample, and the total volume of the reaction mixture was brought up to 99.2 μl with $H_2O$.
3. Ten units (about 0.8 μl) of the T7 Sequenase v2.0 (Amersham Life Science, Cleveland, Ohio) was added. All the components were mixed by gently tapping the outside of the tube and were centrifuged at 12,000 g for 1–2 seconds in a microfuge to move all the liquid to the bottom. The reaction was carried out at 22° C. for 15 minutes. Under the reaction conditions described here the random priming products are approximately 50–400 bps.
4. After 15 minutes at 22° C., the reaction was terminated by cooling the sample to 0° C. on ice. 100 μl of ice-cold $H_2O$ was added to the reaction mixture.
5. The random primed products were purified by passing the whole reaction mixture through Microcon-100 (to remove the template and proteins) and Microcon-10 filters (to remove the primers and fragments less than 40 bases), successively. The retentate fraction (about 65 μl in volume) was recovered from the Microcon-10. This fraction containing the desired random priming products was buffer-exchanged against PCR reaction buffer with the new Microcon-10 further use in whole gene reassembly.

2.4 Random Primed DNA Synthesis with PCR Using the Stoffel Fragment of Taq DNA Polymerase Similar to the Klenow fragment of E. coli DNA polymerase I, the Stoffel fragment of Taq DNA polymerase lacks 5' to 3' exonuclease activity. It is also more thermostable than Taq DNA polymerase. The Stoffel fragment has low processivity, extending a primer an average of only 5–10 nucleotides before it dissociates. As a result of its lower processivity, it may also have improved fidelity.

1. 50 ng (about 0.175 pmol) of R1 DNA and equal amount of R2 DNA dissolved in $H_2O$ was mixed with 6.13 μg (about 1.7 nmol) of $dp(N)_{12}$ random primers.
2. Ten μl of 10× reaction pre-mix [10× reaction pre-mix: 100 mM Tris-HCl, pH 8.3; 30 mM magnesium chloride, 100 mM KCl, and 2 mM each dATP, dCTP, dGTP and dTTP) was added, and the total volume of the reaction mixture was brought up to 99.0 μl with $H_2O$.
3. After incubation at 96° C. for 5 minutes, 2.5 units (about 1.0 μl) of the Stoffel fragment of Taq DNA polymerase (Perkin-Elmer Corp., Norwalk, Conn.) was added. Thirty-five thermocycles were performed, each with 60 seconds at 95° C., 60 seconds at 55° C. and 50 seconds at 72° C., without the extension step of the last cycle, in a DNA Engine PTC-200 (MJ Research Inc., Watertown, Mass.) apparatus. Under the reaction conditions described here the random priming products are approximately 50–500 bp.
4. The reaction was terminated by cooling the sample to 0° C. on ice. 100 μl of ice-cold $H_2O$ was added to the reaction mixture.
5. The random primed products were purified by passing the whole reaction mixture through Microcon-100 (to remove the template and proteins) and Microcon-10 filters (to remove the primers and fragments less than 40 bases), successively. The retentate fraction (about 65 μl in volume) was recovered from the Microcon-10. This fraction containing the desired random priming products was buffer-exchanged against PCR reaction buffer with the new Microcon-10 further use in whole gene reassembly.

2.5 Random Primed DNA Synthesis with PCR Using Pfu DNA Polymerase

Pfu DNA polymerase is extremely thermostable, and the enzyme possesses an inherent 3' to 5' exonuclease activity but does not possess a 5'→3' exonuclease activity. Its base substitution fidelity has been estimated to be $2 \times 10^{-6}$.

1. 50 ng (about 0.175 pmol) of R1 DNA and equal amount of R2 DNA dissolved in $H_2O$ was mixed with 6.13 mg (about 1.7 nmol) of $dp(N)_{12}$ random primers.
2. Fifty μl of 2× reaction pre-mix [2× reaction pre-mix: 5-fold diluted cloned Pfu buffer (Stratagene, La Jolla, Calif.), 0.4 mM each dNTP], was added, and the total volume of the reaction mixture was brought up to 99.0 μl with $H_2O$.
3. After incubation at 96° C. for 5 minutes, 2.5 units (about 1.0 μl) of Pfu DNA polymerase (Stratagene, La Jolla, Calif.) was added. Thirty-five thermocycles were performed, each with 60 seconds at 95° C., 60 seconds at 55° C. and 50 seconds at 72° C., without the extension step of the last cycle, in a DNA Engine PTC-200 (MJ Research Inc., Watertown, Mass.) apparatus. Under the reaction conditions described here the major random priming products are approximately 50–500 bp.
4. The reaction was terminated by cooling the sample to 0° C. on ice. 100 μl of ice-cold $H_2O$ was added to the reaction mixture.
5. The random primed products were purified by passing the whole reaction mixture through Microcon-100 (to remove the template and proteins) and Microcon-10 filters (to remove the primers and fragments less than 40 bases), successively. The retentate fraction (about 65 μl in volume) was recovered from the Microcon-10. This fraction containing the desired random priming products was buffer-exchanged against PCR reaction buffer with the new Microcon-10 further use in whole gene reassembly.

(3) Reassembly of the Whole Gene

1. For reassembly by PCR, 10 μl of the random-primed DNA fragments from Microcon-10, 20 μl of 2× PCR pre-mix (5-fold diluted cloned Pfu buffer, 0.5 mM each dNTP, 0.1 U/μl cloned Pfu polymerase (Stratagene, La Jolla, Calif.)), 15 μl of $H_2O$ were mixed on ice.
2. After incubation at 96° C. for 3 minutes, 40 thermocycles were performed, each with 1.0 minute at 95° C., 1.0 minute at 55° C. and 1.0 minute +5 second/cycle at 72° C., with the extension step of the last cycle proceeding at 72° C. for 10 minutes, in a DNA Engine PTC-200 (MJ Research Inc., Watertown, Mass.) apparatus without adding any mineral oil.
3. 3 μl aliquots at cycles 20, 30 and 40 were removed from the reaction mixture and analyzed by agarose gel electrophoresis. The reassembled PCR product at 40 cycles contained the correct size product in a smear of larger and smaller sizes.

(4) Amplification

The correctly reassembled product of this first PCR was further amplified in a second PCR reaction which contained the PCR primers complementary to the ends of the template DNA.

1. 2.0 μl of the PCR reassembly aliquots were used as template in 100-μl standard PCR reactions, which contained 0.3 mM each primers of P1 (5' CCGAGCGTTGC ATATGTGGAAG 3') (SEQ. ID. NO: 15) and P2 (5' CGACTCTAGAGGATCCGATTC 3') (SEQ. ID. NO: 16), 1.5 mM $MgCl_2$, 10 mM Tris-HCl [pH 9.0], 50 mM KCl, 200 mM each of the four dNTPs, 2.5 U of Taq polymerase (Promega, Madison, Wis., USA) and 2.5 U of Pfu polymerase (Stratagene, La Jolla, Calif.).
2. After incubation at 96° C. for 3 minutes, 15 thermocycles were performed, each with 60 seconds at 95° C., 60 seconds at 55° C. and 50 seconds at 72° C., followed by additional 15 thermocycles of 60 seconds at 95° C., 60 seconds at 55° C. and 50 seconds (+5 second/cycle) at 72° C. with the extension step of the last cycle proceeding at 72° C. for 10 minutes, in a DNA Engine PTC-200 (MJ Research Inc., Watertown, Mass.) apparatus without adding any mineral oil.
3. The amplification resulted in a large amount of PCR product with the correct size of the subtilisin E whole gene.

(5) Cloning

Since the short DNA fragments were generated with five different DNA polymerases, there were five pools of final PCR amplified reassembled products. Each of the DNA pool was used for constructing the corresponding subtilisin E mutant library.

1. The PCR amplified reassembled product was purified by Wizard DNA-CleanUp kit (Promega, Madison, Wis.), digested with BamHI and NdeI, electrophoresed in a 0.8% agarose gel. The 986-bp product was cut from the gel and purified by Wizard PCR Prep kit (Promega, Madison, Wis.). Products were ligated with vector generated by BamHI-Nde1 digestion of the pBE3 shuttle vector.
2. *E. coli* HB101 competent cells were transformed with the above ligation mixture to form a mutant library. About 4,000 transformants from this library were pooled, and recombinant plasmid mixture was isolated from this pool.
3. *B. subtilis* DB428 competent cells were transformed with the above isolated plasmid mixture to form another library of the subtilisin E variants.
4. Based on the DNA polymerase used for random priming the short, nascent DNA fragments, the five libraries constructed here were named: library/Klenow, library/T4, library/Sequenase, library/Stoffel and library/Pfu. About 400 tranformants from each library were randomly picked and subjected to screening for thermostability [see Step (7)].

(6) Random Clone Sequencing

Ten random clones from the *B. subtilis* DB428 library/ Klenow was chosen for DNA sequence analysis. Recombinant plasmids were individually purified from *B. subtilis* DB428 using a QlAprep spin plasmid miniprep kit (QIAGEN) with the modification that 2 mg/ml lysozyme was added to P1 buffer and the cells were incubated for 5 minutes at 37° C., retransformed into competent *E. coli* HB 101 and then purified again using QlAprep spin plasmid miniprep kit to obtain sequencing quality DNA. Sequencing was done on an ABI 373 DNA Sequencing System using the Dye Terminator Cycle Sequencing kit (Perkin-Elmer Corp., Norwalk, Conn.).

(7) Screening for Thermostability

About 400 transformants from each of the five libraries described at Step (4) were subjected to screening. Screening was based on the assay described previously (33, 35), using succinyl-Ala-Ala-Pro-Phe-p-nitroanilide (SEQ. ID. NO: 25) as substrate. *B. subtilis* DB428 containing the plasmid library were grown on LB/kanamycin (20 μg/ml) plates. After 18 hours at 37° C. single colonies were picked into 96-well plates containing 100 μl SG/kanamycin medium per well. These plates were shaken and incubated at 37° C. for 24 hours to let the cells to grow to saturation. The cells were spun down, and the supernatants were sampled for the thermostability assay. Three replica 96-well assay plates were duplicated for each growth plate, with each well containing 10 ml of supernatant. The subtilisin activities were then measured by adding 100 ml of activity assay solution (0.2 mM succinyl-Ala-Ala-Pro-Phe-p-nitroanilide (SEQ. ID. NO: 25), 100 mM Tris-HCl, 10 mM CaCl$_2$, pH 8.0, 37° C.). Reaction velocities were measured at 405 nm over 1.0 min. in a ThermoMax microplate reader (Molecular Devices, Sunnyvale Calif.). Activity measured at room temperature was used to calculate the fraction of active clones (clones with activity less than 10% of that of wild type were scored as inactive). Initial activity (Ai) was measured after incubating one assay plate at 65° C. for 10 minutes by immediately adding 100 µl of prewarmed (37° C.) assay solution (0.2 mM succinyl-Ala-Ala-Pro-Phe-p-nitroanilide (SEQ. ID. NO: 25), 100 mM Tris-HCl, pH 8.0, 10 mM CaCl$_2$) into each well. Residual activity (Ar) was measured after 40 minute incubation.

(8) Sequence Analysis

After screening, one clone that showed the highest thermostability within the 400 transformants from the library/Klenow was re-streaked on LB/kanamycin agar plate, and single colonies derived from this plate were inoculated into tube cultures, for glycerol stock and plasmid preparation. The recombinant plasmid was purified using a QlAprep spin plasmid miniprep kit (QIAGEN) with the modification that 2 mg/ml lysozyme was added to P1 buffer and the cells were incubated for 5 minutes at 37° C., retransformed into competent *E. coli* HB 101 and then purified again using QlAprep spin plasmid miniprep kit to obtain sequencing quality DNA. Sequencing was done on an ABI 373 DNA Sequencing System using the Dye Terminator Cycle Sequencing kit (Perkin-Elmer Corp., Norwalk, Conn.).

Results

Figure 12:
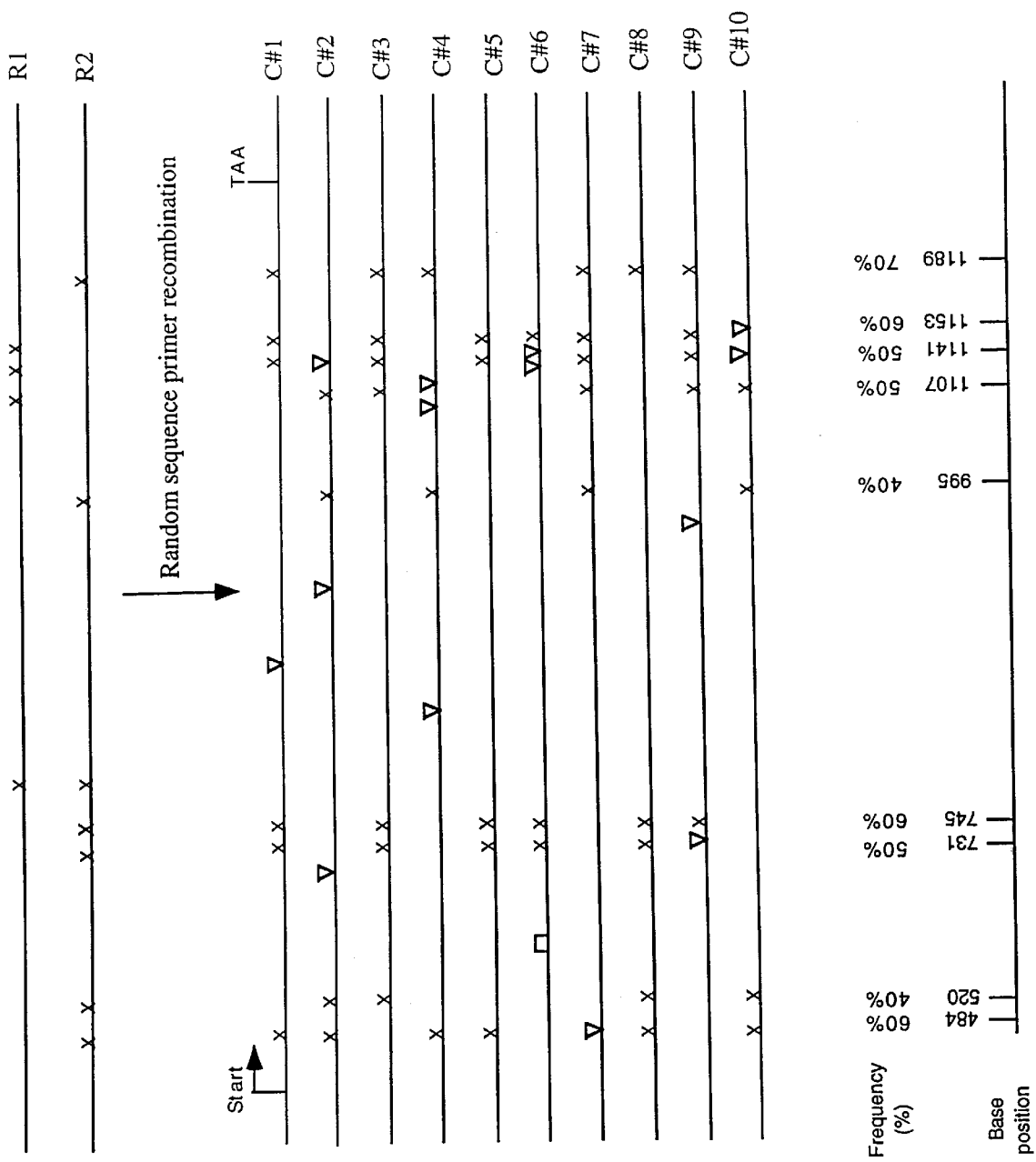
FIG. 12 shows the DNA sequence analysis of 10 clones randomly chosen from the library/Klenow. Lines represent 986-bp of subtilisin E gene including 45 nt of its prosequence, the entire mature sequence and 113 nt after the stop codon. Crosses indicate positions of mutations from R1 and R2, while triangles indicate positions of new point mutations introduced during the random-priming recombination process.
Figure 13A:
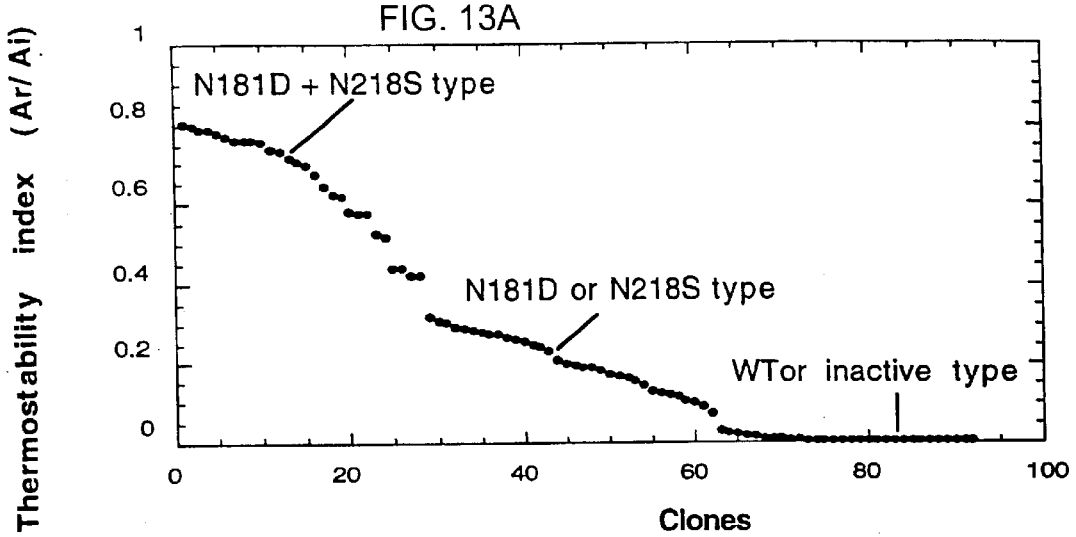
FIGS. 13A, B, C, D and E Thermostability index profiles of the screened clones from the five libraries produced using different polymerases: A) library/Klenow, B) library/T4, C) library/Sequenase, D) library/Stoffel and E) library/Pfu. Normalized residual activity ($A_r/A_i$) after incubation at 65° C. was used as an index of the enzyme thermostability. Data were sorted and plotted in descending order.
Figure 13B:
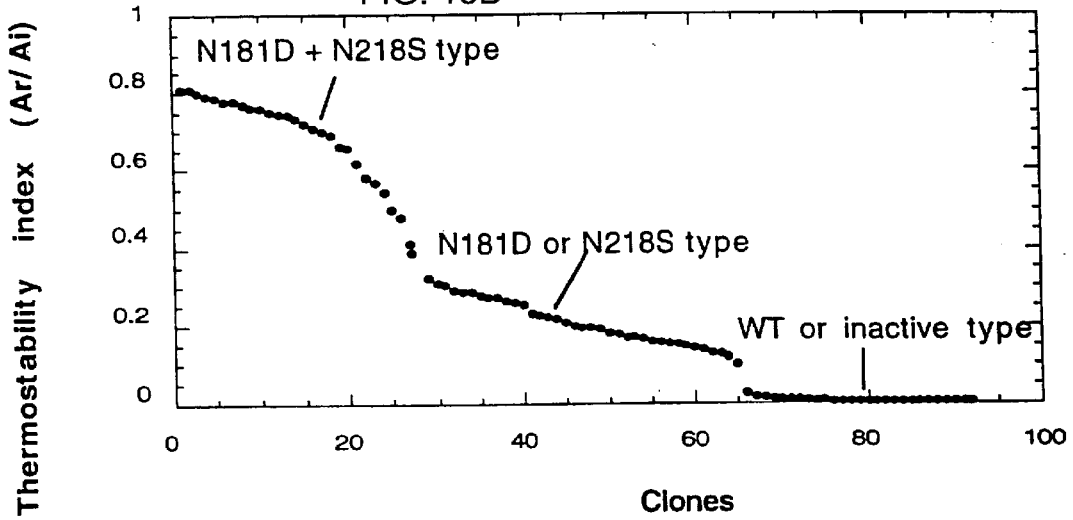
Figure 13C:
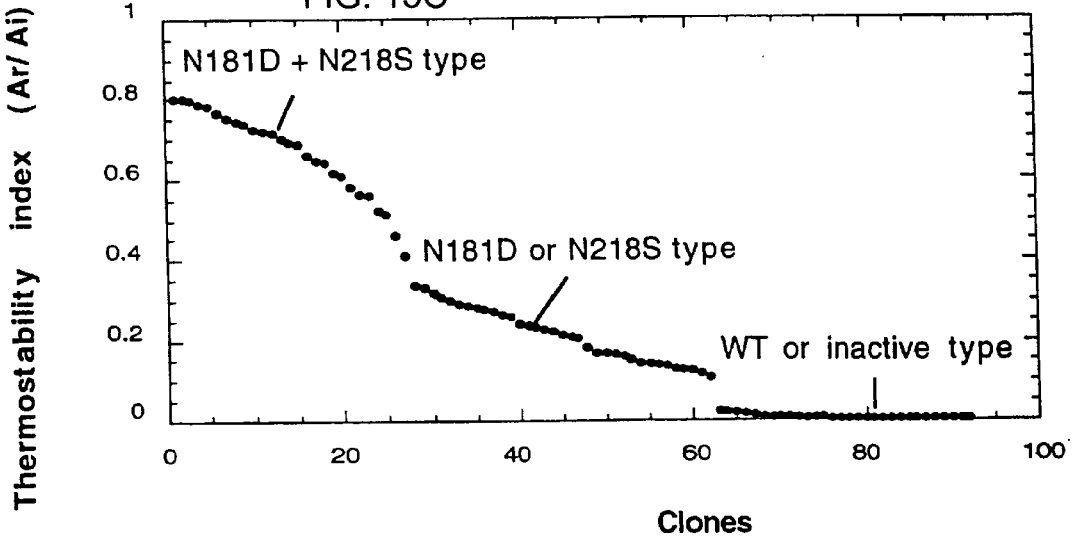
Figure 13D:
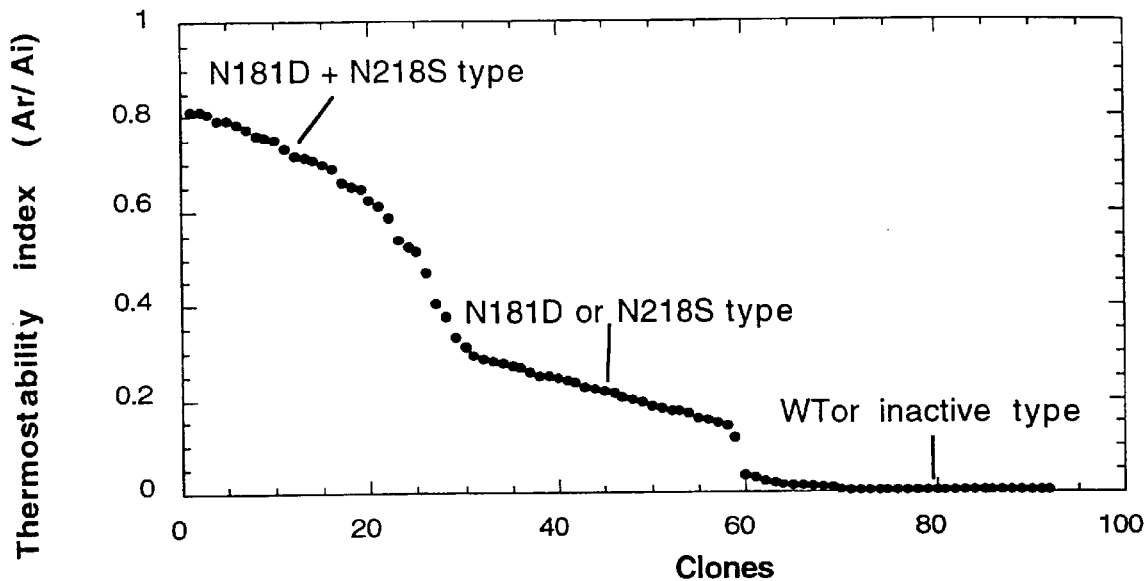
Figure 13E:
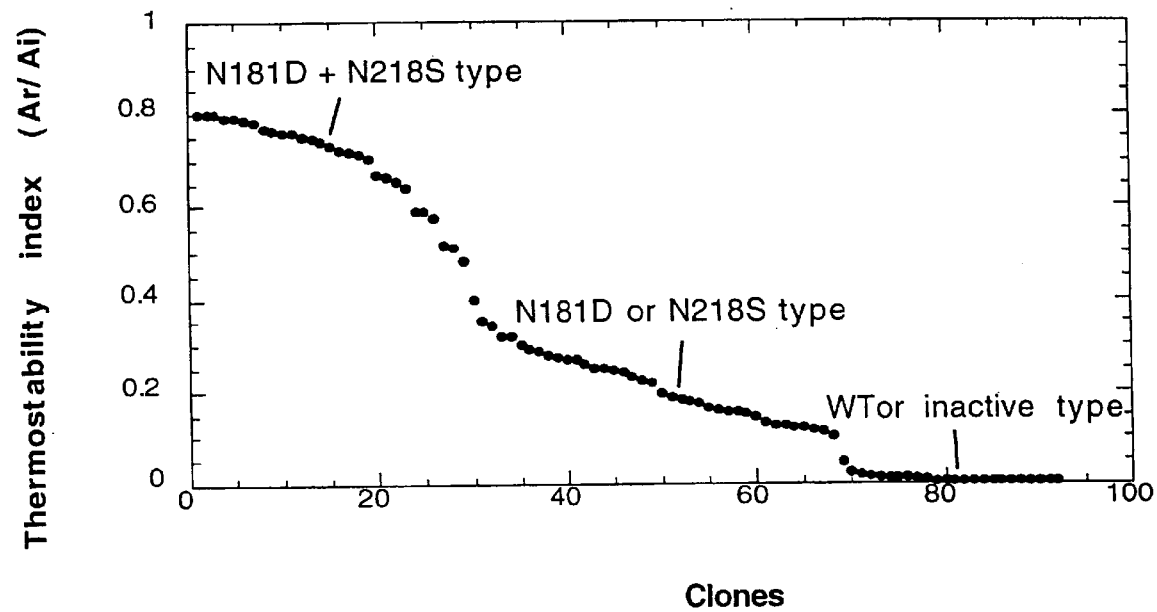

1. Recombination Frequency and Efficiency Associates with the Random-sequence Recombination The random primed process was carried out as described above. The process is illustrated in FIG. 1. Ten clones from the mutant library/Klenow were selected at random and sequenced. As summarized in FIG. 12 and Table 5, all clones were different from the parent genes. The frequency of occurrence of a particular point mutation from parent R1 or R2 in the recombined genes ranged from 40% to 70%, fluctuating around the expected value of 50%. This indicates that the two parent genes have been nearly randomly recombined with the random primer technique. FIG. 12 also shows that all ten mutations can be recombined or dissected, even those that are only 12 bp apart.

We then estimated the rates of subtilisin thermoinactivation at 65° C. by analyzing the 400 random clones from each of the five libraries constructed at Step (5). The thermostabilities obtained from one 96-well plate are shown in FIG. 13, plotted in descending order. Approximately 21% of the clones exhibited thermostability comparable to the mutant with the N181 D and N218S double mutations. This indicates that the N181D mutation from RC2 and the N218S mutation from RC1 have been randomly recombined. Sequence analysis of the clone exhibiting the highest thermostability among the screened 400 transformants from the library/Klenow showed the mutation N181D and N218S did exist.

2. Frequency of Newly Introduced Mutations During the Random Priming Process

Approximately 400 transformants from each of the five *B. subtilis* DB428 libraries [see Step (5)] were picked, grown in SG medium supplemented with 20 ug/ml kanamycin in 96-well plates and subjected to subtilisin E activity screening. Approximately 77–84% of the clones expressed active enzymes, while 16–23% of the transformants were inactive, presumably as a result of newly introduced mutations. From previous experience, we know that this rate of inactivation indicates a mutation rate on the order of 1 to 2 mutations per gene (35).

As shown in FIG. 12, 18 new point mutations were introduced in the process. This error rate of 0.18% corresponds to 1–2 new point mutations per gene, which is a rate that has been determined from the inactivation curve. Mutations are nearly randomly distributed along the gene.

TABLE 5

DNA and amino acid residue substitutions in the ten random clones from Library/Klenow

| Clone # | Position | Base Substitution | Substitution Type | Amino Acid Substitution | Substitution Type |
|---|---|---|---|---|---|
| C#1 | 839 | A→C | transversion | Gly→Gly | synonymous |
| C#2 | 722 | A→G | transition | Ser→Ser | synonymous |
| C#2 | 902 | T→C | transition | Val→Val | synonymous |
| C#2 | 1117 | C→G | transversion | Ser→Ser | synonymous |
| C#4 | 809 | T→C | transition | Asn→Asn | synonymous |
| C#4 | 1098 | G→C | transversion | Gly→Ala | non-synonymous |
| C#4 | 1102 | T→C | transition | Ala→Ala | synonymous |
| C#6 | 653 | C→A | transversion | His→Ile | non-synonymous |
| C#6 | 654 | A→T | transversion | His→Ile | non-synonymous |
| C#6 | 657 | T→C | transition | Val→Ala | non-synonymous |
| C#6 | 658 | A→C | transversion | Val→Ala | non-synonymous |
| C#6 | 1144 | A→G | transition | Ala→Ala | synonymous |
| C#6 | 1147 | A→G | transition | Ala→Ala | synonymous |
| C#7 | 478 | T→C | transition | Ile→Ile | synonymous |
| C#9 | 731 | A→G | transition | Ala→Ala | synonymous |
| C#9 | 994 | A→G | transition | Val→Val | synonymous |
| C#10 | 1111 | A→G | transition | Gly→Gly | synonymous |
| C#10 | 1112 | A→T | transversion | Thr→Ser | non-synonymous |

The mutation types are listed in TABLE 5. The direction of mutation is clearly nonrandom. For example, A changes more often to G than to either T or C. All transitions, and in particular T-C and A-G, occur more often than transversion. Some nucleotides are more mutable than others. One G→C, one C→G and one C→A transversions were found within the 10 sequenced clones. These mutations were generated very rarely during the error-prone PCR mutagenesis of subtilisin (37). Random-priming process may allow access to a greater range of amino acid substitutions than PCR-based point mutagenesis.

It is interesting to note that a short stretch of 5' C GGT ACG CAT GTA GCC GGT ACG 3' (SEQ. ID. NO: 16) at the position 646–667 in parents R1 and R2 was mutated to 5' C GGT ACG ATT GCC GCC GGT ACG 3' (SEQ. ID. NO: 17) in random clone C#6. Since the stretch contains two short repeats at the both ends, the newly introduced mutations may result from a splipped-strand mispairing process instead of point-mutation only process. Since there is no frame-shift, this kind of slippage may be useful for domain conversion.

3. Comparison of Different DNA Polymerase Fidelity in the Random-priming Process During random-priming recombination, homologous DNA sequences are nearly randomly recombined and new point mutations are also introduced. Though these point mutations may provide useful diversity for some in vitro evolution applications, they are problematic recombination of beneficial mutations already identified previously, especially when the mutation rate is this high. Controlling error rate during random priming process is particularly important for successfully applying this technique to solve in vitro evolution problems. By choosing different DNA polymerase and modifying the reaction conditions, the random priming molecular breeding technique can be adjusted to generate mutant libraries with different error rates.

The Klenow fragment of *E. coli* DNA polymerase I, bacteriophage T4 DNA polymerase, T7 sequenase version 2.0 DNA polymerase, the Stoffel fragment of Taq polymerase and Pfu polymerase have been tested for the nascent DNA fragment synthesis. The activity profiles of the resulting five populations [see Step (5)] are shown in FIG. 13. To generate these profiles, activities of the individual clones measured in the 96-well plate screening assay are plotted in descending order. The Library/Stoffel and Library/Klenow contain higher percentage of wild-type or inactive subtilisin E clones than that of the Library/Pfu. In all five populations, percentage of the wild-type and inactive clones ranges from 17–30%.

EXAMPLE 8

Use of Defined Flanking Primers and Staggered Extension to Recombine Single Stranded DNA This example demonstrates the use of the defined primer recombination with staggered extension in the recombination of single stranded DNA.

Method Description

Single-stranded DNA can be prepared by a variety of methods, most easily from plasmids using helper phage. Many vectors in current use are derived from filamentous phages, such as M13mp derivatives. After transformation into cells, these vectors can give rise both to a new double-stranded circles and to a single-stranded circles derived from one of the two strands of the vector. Single-stranded circles are packaged into phage particles, secreted from cells and can be easily purified from the culture supernatant.

Two defined primers (for example, hybridizing to 5' and 3' ends of the templates) are used here to recombine single stranded genes. Only one of the primers is needed before the final PCR amplification. Extended recombination primers are first generated by the staggered extension process (StEP), which consists of repeating cycles of denaturation followed by extremely abbreviated annealing/extension step (s). The extended fragments are then reassembled into full-length genes by thermocycling-assisted homologous gene assembly in the presence of a DNA polymerase, followed by a gene amplification step.

The progress of the staggered extension process is monitored by removing aliquots (10 ul) from the reaction tube (100 ul starting volume) at various time points in the primer extension and separating DNA fragments by agarose gel electrophoresis. Evidence of effective primer extension is seen as appearance of a low molecular weight 'smear' early in the process which increases in molecular weight with increasing cycle number. Initial reaction conditions are set to allow template denaturation (for example, 94° C.-30 second denaturation) followed by very brief annealing/extension step(s) (e.g. 55° C.-1 to 15 seconds) repeated through 5–20 cycle increments prior to reaction sampling. Typically, 20–200 cycles of staggered extension are required to generate single stranded DNA 'smears' corresponding to sizes greater than the length of the complete gene.

The experimental design is as in Example 1. Two thermostable subtilisin E mutants R1 and R2 gene are subcloned into vector M13mp18 by restriction digestion with EcoRI and BamHI. Single stranded DNA is prepared as described (39).

Two Flanking Primer Based Recombination

Two defined primers, P5N (5'-CCGAG CGTTG CATAT GTGGA AG-3' (SEQ. ID. NO: 18), underlined sequence is NdeI restriction site) and P3B (5'-CGACT CTAGA GGATC CGATT C-3' (SEQ. ID. NO: 19), underlined sequence is BamHI restriction site), corresponding to 5' and 3' flanking primers, respectively, are used for recombination. Conditions (100 ul final volume): 0.15 pmol single-stranded DNA containing R1 and R2 gene (mixed at 1:1) are used as template, 15 pmol of one flanking primer (either P5N or P3B), 1× Taq buffer, 0.2 mM of each DNTP, 1.5 mM $MgCl_2$ and 0.25 U Taq polymerase. Program: 5 minutes of 95° C., 80–200 cycles of 30 seconds at 94° C., 5 seconds at 55° C. The single-stranded DNA products of correct size (approximately 1 kb) are cut from 0.8% agarose gel after electrophoresis and purified using QIAEX II gel extraction kit. This purified product is amplified by a conventional PCR. Condition (100 ul final volume): 1–10 ng of template, 30 pmol of each flanking primer, 1× Taq buffer, 0.2 mM of each dNTP, 1.5 mM $MgCl_2$ and 0.25 U Taq polymerase. Program: 5 minutes at 95° C., 20 cycles of 30 seconds at 94° C., 30 seconds at 55° C., 1 minute at 72° C. The PCR product is purified, digested with NdeI and BamHI and subcloned into pBE3 shuttle vector. This gene library is amplified in *E. coli* HB101 and transferred into *B. subtilis* DB428 competent cells for expression and screening, as described elsewhere (35). Thermostability of enzyme variants is determined in the 96-well plate format described previously (33).

This protocol results in the generation of novel sequences containing novel combinations of mutations from the parental sequences as well as novel point mutations. Screening allows the identification of enzyme variants that are more thermostable than the parent enzymes, as in Example 1.

As is apparent from the above examples, primer-based recombination may be used to explore the vast space of potentially useful catalysts for their optimal performance in a wide range of applications as well as to develop or evolve new enzymes for basic structure-function studies.

While the present specification describes using DNA-dependent DNA polymerase and single-stranded DNA as templates, alternative protocols are also feasible for using single-stranded RNA as a template. By using specific protein mRNA as the template and RNA-dependent DNA polymerase (reverse transcriptase) as the catalyst, the methods described herein may be modified to introduce mutations and crossovers into cDNA clones and to create molecular diversity directly from the mRNA level to achieve the goal of optimizing protein functions. This would greatly simplify the ETS (expression-tagged strategy) for novel catalyst discovery.

In addition to the above, the present invention is also useful to probe proteins from obligate intracellular pathogens or other systems where cells of interest cannot be propagated (38).

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

BIBLIOGRAPHY

1. Shao, Z. and Arnold F. H. 1996. Engineering new functions and altering existing functions. Curr. Opin. Struct. Biol. 6: 513–518.
2. Holland, J. H. 1975. Adaption in natural and artificial systems. The University Press, Ann Arbor.
3. Goldberg, D. E. 1989. Genetic algorithms in search, optimization and machine learning. Addison-Wesley. Reading.

4. Eigen, M. 1971. Self-organization of matter and the evolution of biological macromolecules. Naturwissenschaften 58: 465–523.
5. Rechenberg, I. 1973. Evolutionsstrategie: Optimierung technischer Systeme nach Prizipien der biologischen Evolution. Frommann-Holzboog, Stuttgart.
6. Brady, R. M. 1985. Optimization strategies gleaned from biological evolution. Nature 317: 804–806.
7. Muhlenbein, H. 1991. The parallel genetic algorithm as function optimizer. Parallel Computing 17:619–632.
8. Pál, K. F. 1993. Genetic algorithms for the traveling salesman problem-based on a heuristic crossover operation. Bio. Cybern. 69: 539–546.
9. Pál, K. F. 1995. Genetic algorithm with local optimization. Bio.Cybern. 73, 335–341.
10. Joyce, G. F. 1992. Directed molecular evolution. Scientific American, 267:90–97.
11. Arnold, F. H. 1996. Directed evolution—creating biocatalysts for the future. Chem. Eng. Sci. 51:5091–5102.
12. Abelson J N, Ed. 1996. Combinatorial chemistry. *Methods in Enzymology*, 267. Academic Press, Inc., San Diego.
13. Warren M S, Benkovic S J. 1997. Combinatorial manipulation of three key active site residues in glycinamide ribonucleotide transformylase. *Protein Engineering* 10:63–68.
14. Wang C-I, Yang Q, Craik C S. 1996. Phage display of proteases and macromolecular inhibitors. *Methods in Enzymology* 267:52–68.
15. Moore, J. C. and Arnold, F. H. 1996. Directed evolution of a para-nitrobenzyl esterase for aqueous-organic solvents. Nature Biotech. 14: 458–467.
16. Reidhaar-Olson, J. F. and Sauer, R. T. 1988. Combinatorial cassette mutagenesis as a probe of the informational content of protein sequences. Science 241: 53–57.
17. Stemmer, W. P. C. 1994a. Rapid evolution of a protein in vitro by DNA shuffling. Nature, 370: 389–391.
18. Stemmer, W. P. C. 1994b. DNA shuffling by random fragmentation and reassembly -in vitro recombination for molecular evolution. Proc. Natl. Acad. Sci., USA, 91:10747–10751.
19. U.S. Pat. No. 5,605,793.
20. Moore, J. C., H.-M. Jin, O. Kuchner and F. H. Arnold. 1997. Strategies for the in vitro Evolution of Protein Function: Enzyme Evolution by Random combination of Improved Sequences, J. Molecular Biology, in press.
21. Klenow, H. and I. Henningsen. 1970. Selective elimination of the exonuclease activity of the deoxyribonucleic acid polymerase from *Escherichis coli* B by limited proteolysis. Proc. Natl. Acad. Sci. 65:168
22. Feinberg, A. P. and Vogelstein, B. 1983. A technique for radiolabeling DNA restriction endonuclease fragments to high specific activity. Anal. Biochem. 132: 6–13.
23. Nossal, N. G. 1974. DNA synthesis on a double-stranded DNA template by the T4 bacteriophage DNA polymerase and the T4 gene 32 DNA unwinding protein. J. Biol. Chem. 249: 5668–5676.
24. Ehrlich, H. A., PCR Technology, Stockton Press (1989).
25. Oliphant, A. R., Nussbaum, A. L., and Struhl, K. 1986. Cloning of random-sequence oligodeoxynucleotides. Gene 44: 177–183.
26. Hermes, J. D., Blacklow, S. C., and Knowles, J. R. 1990. Searching sequence space by definably random mutagenesis—improving the catalytic potency of an enzyme. Proc. Natl. Acad. Sci. USA 87: 696–700.
27. Leung, D. W., Chen, E., and Goeddel, D. V. 1989. A method for random mutagenesis of a defined DNA segment using a modified polymerase chain reaction. Bio-Technique 1: 11–15.
28. Chen, K. and Arnold, F. H. 1993. Tuning the activity of an enzyme for unusual environments: sequential random mutagenesis of subtilisin E for catalysis in dimethylformamide. Proc. Natl. Acad. Sci. USA 90:5681–5622.
29. Sambrook, J., Fritsch, E. F. and Maniatis, T. 1989. Molecular cloning: A Laboratory Manual. 2nd ed. Cold Spring Harbor Laboratory Press, Cold Spring Harbor, N.Y.
30. Hodgson, C. P. and Fisk R. Z. 1987. Hybridization probe size control: optimized 'oligolabeling'. Nucleic Acids Res. 15:6296.
31. Tabor, S. and Richardson, C. C. 1987. DNA sequence analysis with a modified bacteriophage T7 DNA polymerase. Proc. Natl. Acad. Sci., USA, 84:4767–4771.
32. Tabor, S. and Richardson, C. C. 1989. Selective inactivation of the exonuclease activity of bacteriophage-T7 DNA polymerase by in vitro mutagenesis. J.Biol.Chem. 264:6447–6458.
33. Zhao, H. and Arnold, F. H. 1997. Functional and non-functional mutations distinguished by random recombination of homologous genes. Proc. Natl. Acad. Sci. USA 94:7997–8000.
34. Zock, J., Cantwell, C., Swartling, J., Hodges, R., Pohl, T., Sutton, K., Rosteck Jr., P., McGilvray, D. & Queener, S. 1994. The *Bacillus subtilis* pnbA gene encoding p-nitrobenzyl esterase—cloning, sequence and high-level expression in *Escherichia coli*. Gene, 151, 37–43.
35. Zhao, H. and Arnold, F. H. 1997. Optimization of DNA shuffling for high fidelity recombination. Nucleic Acids Research, 25:1307–1308.
36. Lehman, I. R. and Richardson, C. C. 1964. The deoxyribonucleases of *Escherichia coli*. IV. An exonuclease activity present in purified preparations of deoxyribonucleic acid polymerase. J. Biol. Chem. 239:233.
37. Shafikhani, S., Siegel, R. A., Ferrari, E. & Schellenberger, V. 1997. Generation of large libraries of random mutants in *Bacillus subtilis* by PCR-based plasmid multimerization. Biotechniques, in press.
38. Ebel, T., Middleton, J. F. S., Frisch, A., and Lipp, J. 1997. Characterization of a secretory type Theileria parva glutaredoxin homologue identified by novel screening procedure. J. Biol. Chem. 272 (5): 3042–3048.
39. Messing, J. 1983. Methods Enzymology 101:20–78.
40. Innis, M. A. et al., 1988. Proc. Natl. Acad. Sci. 85:9436–9440.

---

What is claimed is:

1. A method of recombining polynucleotides to produce recombinant polynucleotides, comprising:
    (a) providing a population of different template polynucleotides having different sequences and a pair of first and second primers respectively disposed to hybridize to at least one strand of the template polynucleotides and its complement;
    (b) conducting a multi-cyclic polynucleotide extension reaction on the template polynucleotides primed from the first primer and not the second primer under conditions of incomplete extension, whereby incomplete extension product primed from the first primer anneals to different members of the population of template polynucleotides having different sequences in different extension cycles and undergoes further extension thereby generating recombinant incomplete extension products and subsequently full-length recombinant extension products;
    (c) contacting the full-length recombinant extension products with the second primer and extending the second primer to form double stranded full-length recombinant extension products.

2. The method of claim 1, wherein the template polynucleotides are single stranded.

3. The method of claim 2, wherein the template polynucleotides are of unknown sequence.

4. The method of claim 1, wherein the template polynucleotides comprise allelic variants.

5. The method of claim 1, further comprising amplifying the double stranded full-length recombinant extension product.

6. The method of claim 1, wherein the first primer is extended by an average of fewer than 300 nucleotides per extension cycle.

7. The method of claim 1, wherein the first primer is extended by an average of 20–50 nucleotides per extension cycle.

8. The method of claim 1, wherein the first and second primers are 6–100 nucleotides in length.

9. The method of claim 1, wherein at least one of the first and second primers comprises a random nucleotide at one or more nucleotide positions within the primer.

10. The method of claim 1, further comprising cloning the double stranded full-length recombinant extension products into multiple copies of a vector.

11. The method of claim 1, further comprising screening or selecting the double stranded full-length extension products or expression products thereof for an altered or enhanced property relative to the template polynucleotides or expression products thereof.

12. The method of claim 11, wherein the expression products are screened for an enzymatic activity.

13. The method of claim 1, wherein the template polynucleotides are RNA molecules, and the multi-cyclic polynucleotide extension reaction is conducted with a reverse transcriptase.

14. The method of claim 1, further comprising monitoring the formation of extension product at a plurality of times during the method.

15. A method of recombining polynucleotides to produce recombinant polynucleotides, comprising:

(a) providing a population of different template polynucleotides having different sequences and a pair of first and second primers respectively disposed to hybridize to at least one of the template polynucleotides and its complement;

(b) annealing the first primer to the at least one template polynucleotide;

(c) conducting a template dependent extension of the first primer under conditions of incomplete extension to form an incomplete extension product annealed to the at least one template;

(d) denaturing the incomplete extension product and the at least one template;

(e) annealing the incomplete extension product to at least a second template;

(f) conducting template dependent extension of the incomplete extension product to form a further incomplete or a full-length extension product, which extension product contains sequences extended from a plurality of the different templates having different sequences;

(g) denaturing the extension product of (f) and the template to which it is annealed;

(h) performing further cycles of (e–g) if needed to produce a full-length extension product;

(i) annealing the second primer to the full-length extension product of step (h), and extending the second primer to form a double stranded full-length extension product, the extension product being a recombined form of the template polynucleotides.

16. A method of recombining polynucleotides having different sequences, comprising:

performing in vitro recombination of first strands of a population of template polynucleotides having different sequences without recombining second strands complementary to the first strands;

synthesizing complementary strands to the recombined first strands to form recombined duplex polynucleotides.

17. The method of claim 16, wherein the different template polynucleotides are provided in single stranded form before performing the in vitro recombination.

18. The method of claim 16, wherein the different template polynucleotides are provided in double stranded form before performing the in vitro recombination.

19. The method of claim 16, wherein the different template polynucleotides comprise allelic variants.

20. The method of claim 16, further comprising amplifying the recombined duplex polynucleotides.

21. The method of claim 20, further comprising cloning the amplified recombined duplex polynucleotides into multiple copies of a vector.

22. The method of claim 16, further comprising screening or selecting the recombined duplex polynucleotides or expression products thereof for an altered or enhanced property relative to the template polynucleotides or expression products thereof.

23. The method of claim 22, wherein the expression products are screened or selected for an enzymatic activity.

24. The method of claim 16, wherein the template polynucleotides are of unknown sequence.

25. The method of claim 16, further comprising screening or selecting the recombined duplex polynucleotides or expression products thereof in a plate-based assay.

26. The method of claim 25, further comprising amplifying the recombined duplex polynucleotides.

27. The method of claim 26, further comprising cloning the amplified recombined duplex polynucleotides into multiple copies of a vector.

28. The method of claim 27, wherein the vector is a plasmid.

29. The method of claim 25, wherein the expression products are screened or selected for an enzymatic activity.

30. The method of claim 29, wherein the plate comprises a substrate for the enzymatic activity.

31. The method of claim 30, wherein the expression products are screened or selected for subtilisin activity.

32. The method of claim 30, wherein the expression products are screened or selected for deacylase activity.

33. The method of claim 28, wherein the expression products are screened or selected for an enzymatic activity.

34. The method of claim 33, wherein the plate comprises a substrate for the enzymatic activity.

35. The method of claim 34, wherein the expression products are screened or selected for subtilisin activity.

36. The method of claim 34, wherein the expression products are screened or selected for deacylase activity.

37. The method of claim 23, wherein the expression products are screened or selected for subtilisin activity.

38. The method of claim 23, wherein the expression products are screened or selected for deacylase activity.

39. The method of claim 16, wherein the in vitro recombination is performed with a mesophilic polymerase lacking strand displacement activity.

40. The method of claim 39, wherein said mesophilic polymerase lacking strand displacement activity is a bacteriophage DNA polymerase.

41. The method of claim 39, wherein the bacteriophage DNA polymerase is selected from the group consisting of T4 DNA polymerase and T7 Sequenase DNA polymerase.

* * * * *